(12) United States Patent
Solem

(10) Patent No.: US 9,155,479 B2
(45) Date of Patent: Oct. 13, 2015

(54) INTRA CARDIAC DEVICE, SYSTEM AND METHODS

(75) Inventor: Jan Otto Solem, Stetten (CH)

(73) Assignee: Tor Peters, Herrliberg (CH)

( * ) Notice: Subject to any disclaimer, the term of this patent is extended or adjusted under 35 U.S.C. 154(b) by 1859 days.

(21) Appl. No.: 12/097,033

(22) PCT Filed: Dec. 12, 2005

(86) PCT No.: PCT/EP2005/056700
§ 371 (c)(1),
(2), (4) Date: Sep. 5, 2008

(87) PCT Pub. No.: WO2007/068284
PCT Pub. Date: Jun. 21, 2007

(65) Prior Publication Data
US 2009/0171408 A1    Jul. 2, 2009

(51) Int. Cl.
*A61B 5/0245* (2006.01)
*A61N 1/365* (2006.01)
*A61N 1/378* (2006.01)
*A61B 5/00* (2006.01)
*A61N 1/362* (2006.01)
*A61N 1/372* (2006.01)

(52) U.S. Cl.
CPC .......... *A61B 5/0245* (2013.01); *A61N 1/36542* (2013.01); *A61N 1/3785* (2013.01); *A61B 5/0031* (2013.01); *A61N 1/3627* (2013.01); *A61N 1/37205* (2013.01)

(58) Field of Classification Search
CPC ............... A61B 5/0245; A61B 2560/0214; A61N 1/3785; A61N 1/36542; H02N 2/18
USPC .......................................................... 607/35
See application file for complete search history.

(56) References Cited

U.S. PATENT DOCUMENTS

| 3,456,134 A | 7/1969 | Ko |
| 3,835,864 A | 9/1974 | Rasor et al. |
| 4,798,206 A | 1/1989 | Maddison et al. |
| 5,103,837 A | 4/1992 | Weidlich et al. |
| 5,431,694 A | 7/1995 | Snaper et al. |
| 6,047,214 A * | 4/2000 | Mueller et al. .................. 607/61 |
| 6,328,699 B1 | 12/2001 | Eigler et al. |
| 6,654,638 B1 | 11/2003 | Sweeney |
| 2003/0158584 A1 | 8/2003 | Cates et al. |
| 2005/0055061 A1 | 3/2005 | Holzer |
| 2005/0256549 A1 * | 11/2005 | Holzer ............................ 607/35 |

FOREIGN PATENT DOCUMENTS

EP    1 541 191 A    6/2005

* cited by examiner

*Primary Examiner* — Tammie K Heller
(74) *Attorney, Agent, or Firm* — Inskeep IP Group, Inc.

(57) ABSTRACT

An intra cardiac device transforms kinetic energy from heart tissue movement into electrical energy to power the device and provide information in respect of heart function. A system comprising such an intra cardiac device may communicate wirelessly with at least one receiver outside the body and may be used for conveniently monitoring or stimulating a patient's heart.

28 Claims, 24 Drawing Sheets

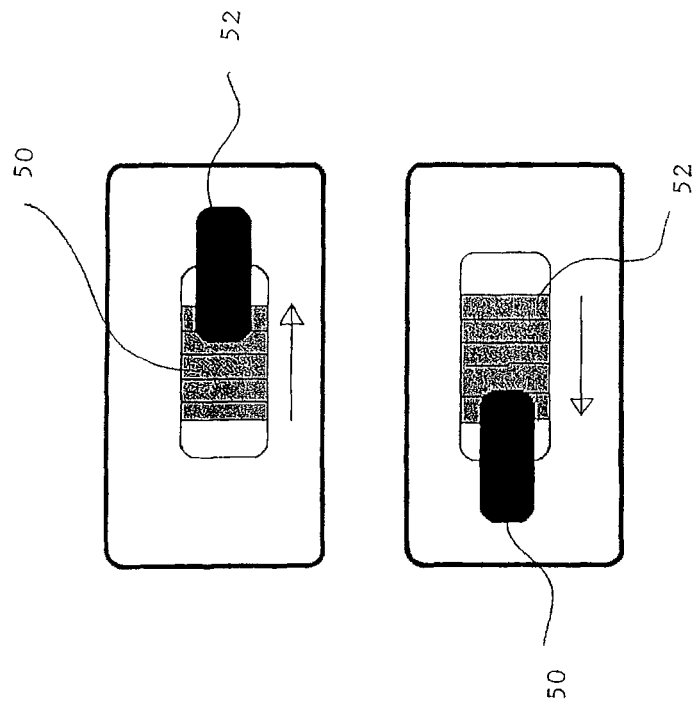
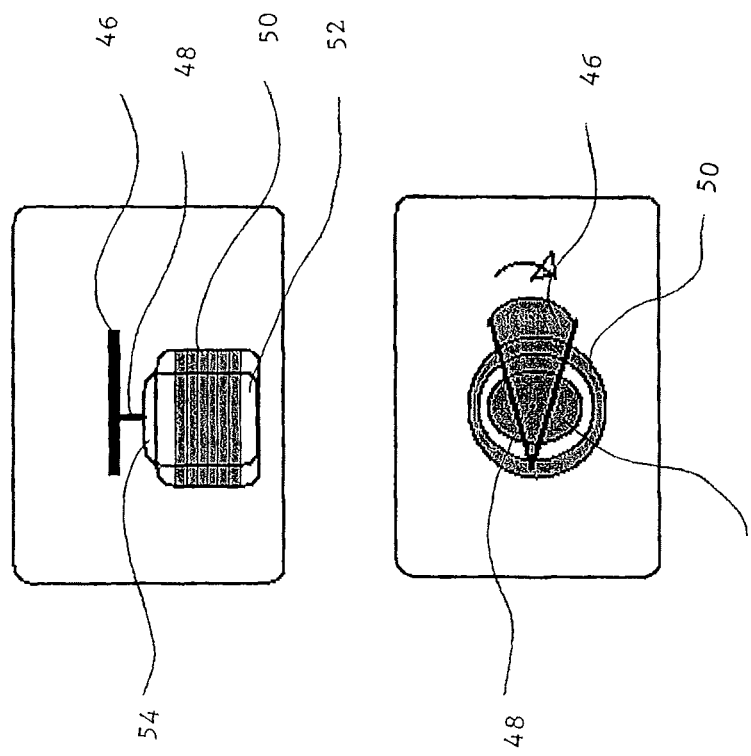
Fig. 4a
Fig. 4b

INTRA CARDIAC DEVICE, SYSTEM AND METHODS

RELATED APPLICATIONS

The present invention claims benefit of International Application No. PCT/EP2005/056700, filed 12 Dec. 2005, entitled Intra Cardiac Device, System And Methods, which is incorporated herein by reference.

FIELD OF THE INVENTION

The present invention refers to an intra cardiac device and methods for heart function intervention, such as monitoring and controlling of said heart function.

BACKGROUND OF THE INVENTION

Congestive heart failure (CHF) is a condition where the heart is not able to pump enough blood to supply the body with energy and oxygen. There are multiple causes for the heart to fail, such as ischemic heart disease caused by clogged arteries, cardiomyopathy of unknown reasons or end stage after congenital heart diseases or heart valve diseases. With an increasing aging of the population today, the problem of CHF is increasing and is now the most common cause of heart disease mortality. According to the American Heart Association 5 million people in the United States experience CHF, increasing in number by half a million every year. 1% of the population over 50 years of age or 5% of the more than 75 years old are affected by the condition of CHF. Worldwide the number of people suffering from CHD is estimated around 20 million. Independent of what the reason for CHD, the symptoms and the treatment are the same. The failing pump function causes low blood pressure and low cardiac output resulting in renal failure, and a lower urine production causes fluid retention in the body.

A failing left ventricle of the heart causes the blood to be stagnant in the lungs, causing slow flow and high pressures in the blood stream of the lungs. As a result thereof, fluid will be pressed from the blood vessels into the lung tissue resulting in a decreased gas exchange in the lungs, a condition that worsens the heart condition.

A right heart failure on the other hand causes slow flow and stagnation of blood in the vein system of the body. As a result thereof, fluid is pressed from the small blood vessels, the capillaries, into the various organ tissues including the fatty tissue under the skin. This fluid retention causes for instance weight gain, swollen organs and legs and shortness of breath.

The treatment of CHF is first of all a correction of the underlying causes such as valvular disease or coronary artery blocks. However, for the majority of patients this treatment is too late. Surgically, only heart transplantation and implantation of mechanical heart assist devices are available. However, only 2-3000 heart transplants are made worldwide in the youngest population, due to lack of donor organs. Also, mechanical assist devices are still experimental. Therefore the majority of the patients are left with symptomatic medical treatment. First of all fluid restriction and treatment with diuretics are used. Other drugs are Angiotensin-converting Enzyme (ACE) inhibitors, beta-blockers and digitalis. Most of CHF patients live for a long time before dying and are readmitted again and again in order to adjust medication or get diuretics injected. Changes in the heart movements, the volumes and the pressures occur fast. The symptoms, however, appear slowly, resulting in treatment too late.

Previously, Medtronic Inc. has introduced the Chronicle device, an implantable Hemodynamic Monitor. That system contains a Lithium battery and a computing element to be implanted under the skin, remote from the heart. Further, this unit has a lead with a pressure transducer that extends into the heart where it can measure intra cardiac pressure, an indirect indicator when diagnosing a heart condition. The Chronicle unit is capable of using several algorithms to present curves and trends that can be detected in a receiver outside the body.

Savacor Inc. has developed the HeartPOD™, a very similar product to the Chronicle device, the major difference being that the transducer located at the tip of a lead is implanted in the atrial septum wall measuring the pressure in the left atrium. A handheld computer serves as a patient monitor receiving physiological signals from an implant by wireless transmission. Savacor's technology is based on apparatus and methods as described in U.S. Pat. No. 6,328,699.

U.S. Pat. No. 6,328,699 discloses an apparatus for treating congestive heart failure in a patient. However, this apparatus is provided with a pressure transducer lead that is permanently implanted in the left atrium of the patients heart. This pressure transducer lead is connected to an electrical circuitry for processing electrical signals. Thus, the apparatus according to U.S. Pat. No. 6,328,699 has the disadvantage of presenting a lead (or wire) inside the body (and inside the heart) of the patient, rendering the apparatus inferior in respect of a device in no need of such a lead, said device being fully implantable in the body of the patient. Moreover, the device according to U.S. Pat. No. 6,328,699 receives energy from a battery, which renders it inferior inn comparison to a device in no need of a battery.

Remon Medical Technologies Inc. has introduced a device for non-invasive assessment of pulmonary artery pressure. A pressure transducer is inserted into the pulmonary artery and fixed there. The pressure transducer is connected to an implanted remote device collecting data from the implanted transducer. Ultrasound energy is applied from outside the body in order to activate and energize the device. Wireless communication to an external unit is also supported when the device is powered-up.

CardioMEMS Inc. on the other hand has developed a similar system that can measure pressure by means of an un-powered, permanently implantable pressure sensor, which is energized by means of high frequency radio waves from outside the body. The pressure sensor is intended for measuring intrasac pressure during endovascular abdominal aortic aneurysm (AAA) repair.

Disturbances of the Heart Rhythm

Pacemakers (PM) are electronic devices to be implanted in a human body with the purpose to regulate the heart beat and the heart rhythm by means of electrical stimuli in patients that have lost the ability to regulate the heart rhythm, e.g. a heart block is such a condition. A PM 36, e.g. shown in FIG. 2, is a hermetically sealed metal can 38 that contains a battery 40 and an electronic circuit. The PM can is implanted in the body under the skin at a remote site from the heart. The PM delivers electrical stimuli to the heart by means of an electrical lead 42, or multiple electrical leads 42, extending from the PM can 38 in one end to a heart tissue and in the other end having an un-insulated electrode tip 44 or another form of transducer at tip 44, respectively.

Rune Elmqvist, a Swedish engineer designed the first implantable PM, and Dr. Aake Senning implanted the device into the body of the patient Arne Larsson in 1958. The patient lived for 43 years after the first implant and had additionally 23 different PMs implanted during his lifetime. This first PM had a battery that was rechargeable, the first non rechargeable PM was developed simultaneously by Dr. Greatbach in USA and was implanted for the first time in 1960. Today only non-rechargeable PMs are used. The PM industry today is among the most profitable in the medical device area, more than 600,000 PMs are produced yearly. Some modern PMs are able also to detect irregular, sometimes life-threatening irregularities in the heart rhythm, also known as arrhythmia. Over time, PMs were combined with a defibrillator, called an implantable cardioverter defibrillator (ICD), to correct such arrhythmia by means of an electrical shock.

Generally, there are two main problems with PM treatment today, related to the leads and to the battery.

The leads are insulated cables, connected hermetically sealed to the electronic circuit in the PM can in one end and connected to the heart tissue with an un-insulated end, the electrode tip, in the other end. The tip is made of material that facilitates in-growth in the heart tissue. The insulation is made of medical quality polymers, usually polyurethane and is made as thin as possible in order to save space. The insulation must be absolutely impermeable. If not, electrical leak currents will occur and the PM will not function. The core of the lead, the electrically conducting part, is made of a metal that is a good electrical conductor. Since the heart is constantly bending and twisting, the metal in the conductor has to be very tolerant to bending without fracturing, a fracture occurs frequently and stops the electron transfer and the PM does not function. Lead infection is another large problem. Furthermore, the leads are immersed in the blood stream, a perfect environment for bacteria, and in contact with subcutaneous tissue, a common site for infections, especially from the PM can pocket. Bacteria easily migrate from the skin to subcutaneous tissue and into the blood stream along the leads. Finally lead tips often dislocate from the heart tissue, loosing contact to the heart cells, and thereby no electron transfer to the heart tissue is possible. Insulation defects, conductor fracture, infections, and tip dislocations are some of the PM related issues that result in recurrent surgical operations, usually including additional leads being put in, since retrieval of previously implanted leads is very difficult if not impossible in many cases. Thus patients normally end up having many leads, most of them not in use. When more complex devices are used, like an ICD or a PM that stimulates and detects at different sites in the heart (e.g. atrium and ventricle) a system may consist of up to four leads at implant, each of them prone to the problems described above.

The Battery

Different energy sources have been explored for batteries, inclusive nuclear. However, only Lithium (Li) batteries have proven to function well in PMs and today this energy source is exclusively used. Like all batteries the main problem is durability. The electrons will only flow through a closed circuit, from the negative pole of a battery through the load, i.e. the body, back to the positive pole of a battery, and then through the battery (electrical current is described in the opposite direction). Electrons returning to the battery join with Iodine and then with Lithium to Lithium-Iodine (LiI), which is not a good electron conductor. Buildup of LiI increases the internal resistance in a Li battery. Increasing internal resistance causes a decreasing battery voltage and finally the available voltage becomes insufficient to stimulate the heart and the battery is useless. A Li battery will deliver at its beginning-of-life around 2.8 V and in the best case it will have a linear output for 5 years. From this time the internal resistance increases exponentially, and when the voltage comes down to close to the heart stimulation threshold, the battery has to be replaced. A Li battery will normally contain 2 Ah (ampere-hours) of capacity, the drain is typically 25-microamperes, giving a battery a theoretical lifetime of 80 000 hours. In reality, however, they seldom last longer than 5 years.

As one may see, the main problems related to PM treatment are related to the battery and to the leads.

Several attempts have been made to solve these problems.

For instance, W. H. Ko, in U.S. Pat. No. 3,456,134, as published Jul. 15, 1969, discloses a piezoelectric converter for converting body motion to electrical energy for driving electrical implants, such as a PM. Ko found that this piezoelectric system may deliver enough energy to run a PM when driven at a mechanical pulse rate and with a motion similar to the heart motion of an animal, upon which it was tested. However he did neither suggested to integrate a piezoelectric system in a PM itself nor to implant such a conversion device in a heart. As nearly 40 years have passed since the disclosure of Ko, and no commercially available PMs using Kos principle have become available, it is regarded that the skilled person in the field of implanted devices does not regard that it is feasible to carry out Kos piezoelectric system with implantable devices.

U.S. Pat. No. 6,654,638 discloses ultrasonically activated electrodes that generally use a piezoelectric energy converter to convert energy from an external energy source, e.g. an ultrasonic element. This energy is stored within the electrode. It is also mentioned that the electrodes may use the contracting heart to produce energy by compressing or deflecting a piezoelectric element. However, the electrodes disclosed in U.S. Pat. No. 6,654,638 are always controlled by an external device. That means pacing action is not possible by the electrode itself without the interaction with an external control unit. Furthermore, also the piezoelectric element is integrated into the housing of the electrode, whereby the piezoelectric element uses valuable space of the housing's surface that no longer is available for use as an electrode surface.

Hence, there is a need for a device which alleviates or avoids problems such as, but not limited to, those mentioned above, and which device is fully implantable in the body, such as in the vicinity of, or inside, the heart, of a patient, which device may be used for instance for CHF cases, but also in acute situations in the intensive care unit for patients suffering from acute heart failure, for instance after large myocardial infarctions, after catheter based coronary artery operation or after cardiac surgery, which device is in no need of battery (or batteries) or lead(s), which device may continuously monitor the heart function and may initiate early medical counter measures.

SUMMARY OF THE INVENTION

Accordingly, the present invention preferably seeks to mitigate, alleviate or eliminate one or more of the deficiencies in the art and disadvantages, such as the above-identified, but not limited to, singly or in any combination, and solves problems, such as the above-identified, but not limited to, by providing a device according to the appended patent claims.

For this purpose an intra cardiac device of this kind according to claim 1, is characterized by means for transforming kinetic energy from heart muscle movement into electrical energy in use, from which electrical energy information in respect of heart function is obtainable.

Advantageous features of the invention are defined in the dependent claims.

More specifically, according to a first aspect of the invention, an intra cardiac device for heart function intervention is provided that comprises means for transforming kinetic energy from heart tissue movement into electrical energy in use, from which electrical energy information in respect of heart function is obtainable.

The means for transforming kinetic energy into electrical energy may be a magnet, movable relative a coil.

The means for transforming kinetic energy into electrical energy may be a rotatable pendulum, communicating with a magnet, rotatable relative a coil.

The means for transforming kinetic energy into electrical energy may be a piezo-electric energy converter.

The intra cardiac device may comprise an energy storage means, such as a capacitor, adapted to store the transformed electrical energy for use by the intra-cardiac device.

The intra cardiac device may comprise a wireless transmitter or transceiver.

The intra cardiac device may comprise fixation means, for attachment of said device in or at the heart, such as a stent, tines or hooks, or a screw.

The intra cardiac device may comprise elutionable steroids.

The intra cardiac device may be configured to provide device function related data, such as administrative data, programmed data like mode, cardiac stimulation pacing rate, defibrillation energy, power unit condition.

The information may be information in respect of heart function such as measured data like heart rate, heart movement amplitude, heart movement acceleration, electrical heart rate, electrical signal amplitude, or data related to previous cardiac events stored in the intra cardiac device.

The intra cardiac device may be an electrical cardiac stimulator device, such as an implantable pacemaker, a cardioverter defibrillator or a defibrillator.

The intra cardiac device may comprise at least one electronic circuit.

The electronic circuit may comprise pacing algorithms and/or defibrillating algorithms.

The intra cardiac device may comprise a positive and a negative electrode.

The positive and a negative electrode may be configured to obtain electrical heart signals.

The electrical energy may in use of the intra cardiac device be stored in an energy storage means, wherein the energy storage means may be configured to provide energy stored therein for cardiac stimulation via said positive and negative electrode when electrical heart signals are not obtained via said positive and negative electrode.

The poles may be made of good electrically conducting material.

The poles may be made of copper or steel or a polymer.

At least one of said poles may be covered with porous material.

The porous material may be activated carbon, sintered platinum-iridium or sputtered titanium-nitride.

The heart tissue may be a heart muscle.

The intra cardiac device may be a leadless (no external lead as conventionally known) and batteryless self-contained intra cardiac monitoring and/or intra cardiac stimulating heart device capable of wireless communication with other intra cardiac or extracorporeal devices.

According to a second aspect of the invention, a system is provided. The system comprises at least one intra cardiac device according to the first aspect of the invention, and at least one receiver, wherein the at least one intra cardiac device comprises means of communication, through which said at least one device may communicate wirelessly with said at least one receiver.

The at least one receiver may be an extracorporeal receiver located outside a patients body in use of said system having said at least one intra cardiac device implanted therein.

The at least one receiver may be located in a mobile terminal such as a mobile telephone, a fix-net telephone, an intensive care monitor, a pacemaker, a defibrillator, an infusion pump, or a transceiver of a telemetry system.

The system may comprise a plurality of said intra cardiac devices and a first intra cardiac device of said plurality of intra cardiac devices may be configured to communicate with a receiver located in a second intra cardiac device of said plurality of intra cardiac devices.

The intra cardiac device of the system may be configured to communicate information in respect of heart function derived from electrical energy information originated during conversion from kinetic heart movement energy to electrical energy to the receiver.

The means of communication may be wireless communication selected from the group comprising of wireless radio transmission including Bluetooth® or ZigBee®, and ultrasound communication, or combinations thereof.

The system may further comprise a delivery system for an intra cardiac device, wherein the delivery system comprises an intra cardiac device according to the first aspect of the invention, an introducer sheath (78), a guide wire (76), a diagnostic catheter (102), and a delivery catheter (94).

According to another aspect of the invention, a method of communication between a first intra cardiac device according to the first aspect of the invention and a receiver is provided. The method comprises transforming kinetic energy from heart tissue movement into electrical energy, deriving information obtained from said transformed electrical energy related to said heart movement, and communicating said information to said receiver wirelessly.

The method may further comprise using said information to electrically instruct a second intra cardiac device.

The method may further comprise using said information in an external data assembly equipment for monitoring said heart movement.

According to yet another aspect of the invention, a method for monitoring heart function is provided. The method comprises converting kinetic energy from heart tissue movement to electrical energy, and using information related to said electrical energy as an indicator of said heart function.

The method may further comprise wirelessly communicating said information related to the electrical energy to a receiver for interpretation.

The receiver may be located in an external data assembly equipment outside of the patient body.

The external data assembly equipment may be a mobile terminal such as a mobile telephone, or a fix-net telephone line, an intensive care monitor, an infusion pump or a transceiver of a telemetry system.

According to still another aspect of the invention, a method of treatment of heart blocks and arrhythmias is provided. The method comprises transforming kinetic energy from heart tissue movement into electrical energy, and deriving information obtained from said transformed electrical energy related to said heart movement, by the use of at least one intra cardiac device according to a first aspect of the invention; and obtaining electrical heart signals from said at least one intra cardiac device, and stimulating the heart electrically by at least one intra cardiac device with at least a part of the transformed electrical energy.

The first intra cardiac device may communicate with at least a second intra cardiac device.

The first intra cardiac device may act as a master device and the at least second intra cardiac device may act as a slave device.

According to yet a further aspect of the invention, a method of monitoring congestive heart failure is provided. The method comprises transforming kinetic energy from heart tissue movement into electrical energy by the use of at least one intra cardiac device according to a first aspect of the invention, deriving information obtained from said transformed electrical energy related to said heart movement, and communicating said information to a receiver wirelessly.

According to yet another aspect of the invention, a method for positioning a system comprising any of the intra cardiac devices according a first aspect of the invention is provided. The method comprises positioning said intra cardiac device in the right ventricle (RV), in the middle cardiac vein or in the coronary sinus, positioning a second intra cardiac device inside the LV from the aorta, in the lateral marginal veins, in the great cardiac vein or in the coronary sinus, and positioning a third intra cardiac device inside the wall of the right atrium or right atrium appendage, wherein each of these intra cardiac devices implemented as units in a system will communicate with each other.

The method may further comprise positioning a fourth intra cardiac device, implemented as a defibrillator, inside the RV, the marginal veins, the great cardiac vein 4, the coronary sinus 2 or in the middle cardiac vein 10, which fourth intra cardiac device also will communicate with said first, second, and/or third intra cardiac device.

The intra cardiac devices may be attached to the heart surface directly for optimizing positioning, according to the method.

BRIEF DESCRIPTION OF THE DRAWINGS

These and other aspects, features and advantages of which the invention is capable of will be apparent and elucidated from the following description of embodiments of the present invention, reference being made to the accompanying drawings, in which

FIG. 4 *a*) is a schematic illustration showing an intra cardiac device producing electricity by means of induction;

FIG. 4 *b*) is a schematic illustration showing another intra cardiac device producing electricity by means of induction;

FIG. 5 *b*) is a schematic illustration showing a screw as fixation means for an intra cardiac device;

FIG. 5 *c*) is a schematic illustration showing a stent as fixating means for an intra cardiac device, the stent pushing the device against a vessel wall and still leaving the lumen open for sufficient flow;

FIG. 6 *b*) is a schematic illustration showing an intra cardiac device according to an embodiment of the invention having a fixation screw;

FIG. 7 *b*) is a schematic illustration showing an intra cardiac device according to an embodiment of the invention delivered and fixed in the lateral marginal vein;

FIG. 7 *c*) is a schematic illustration showing an intra cardiac device according to an embodiment of the invention delivered and fixed in the middle cardiac vein;

FIG. 7 *d*) is a schematic illustration showing an intra cardiac device according to an embodiment of the invention delivered and fixed in the right ventricle;

FIG. 7 *e*) is a schematic illustration showing an intra cardiac device according to an embodiment of the invention delivered and fixed in the left ventricle;

FIG. 7 *f*) is a schematic illustration showing an intra cardiac device according to an embodiment of the invention delivered and fixed on the heart surface;

FIG. 10 *b*) is a schematic illustration showing access to the vein system through the femoral vein;

FIG. 10 *c*) is a schematic illustration showing access to the left ventricle through the femoral artery;

FIG. 14 *b*) is a schematic illustration showing an intra cardiac device according to an embodiment of the invention delivered in the great cardiac vein by means of a stent.

EMBODIMENTS OF THE INVENTION

Figure 1:
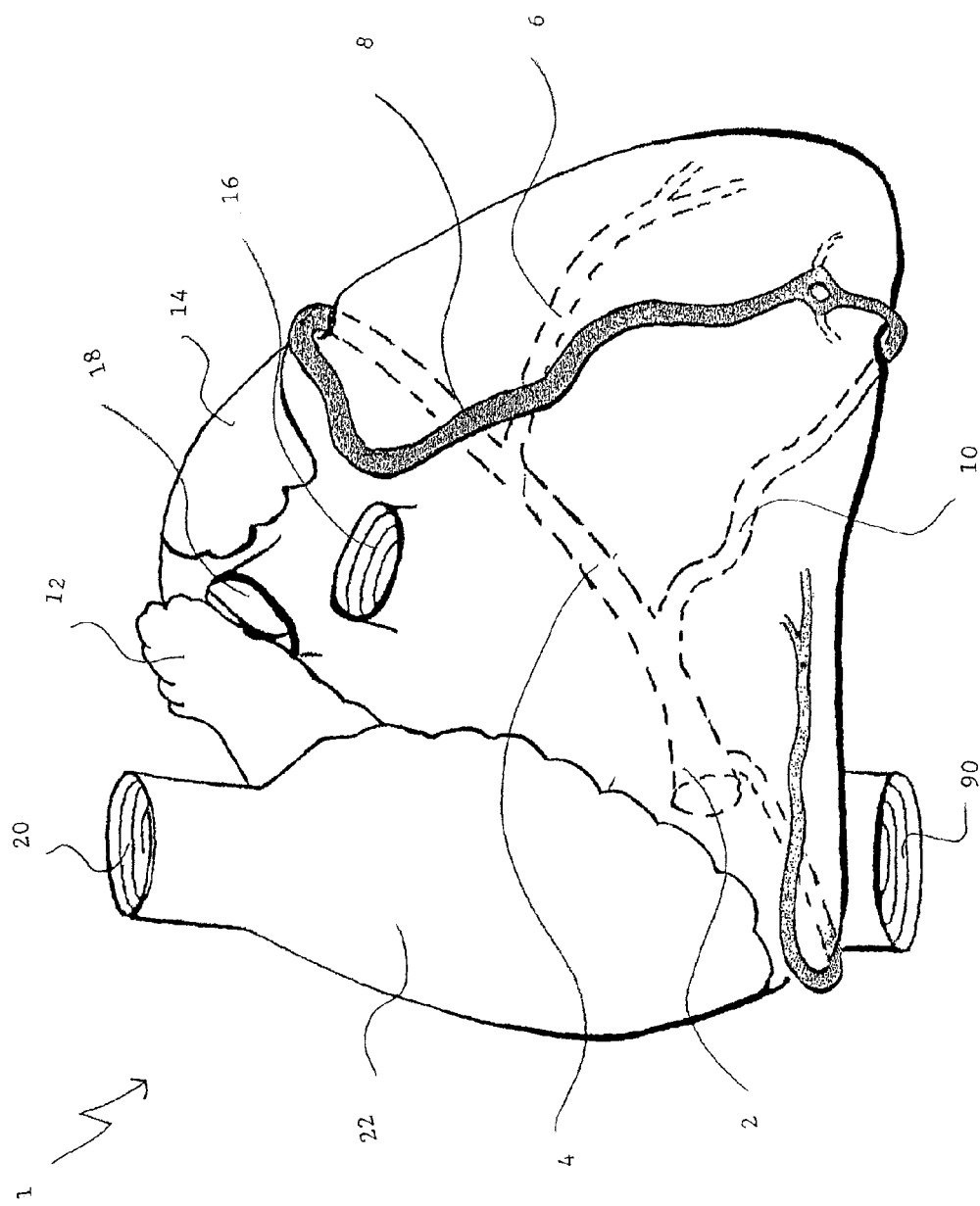
FIG. 1 is a schematic illustration showing a human heart.
Figure 2:
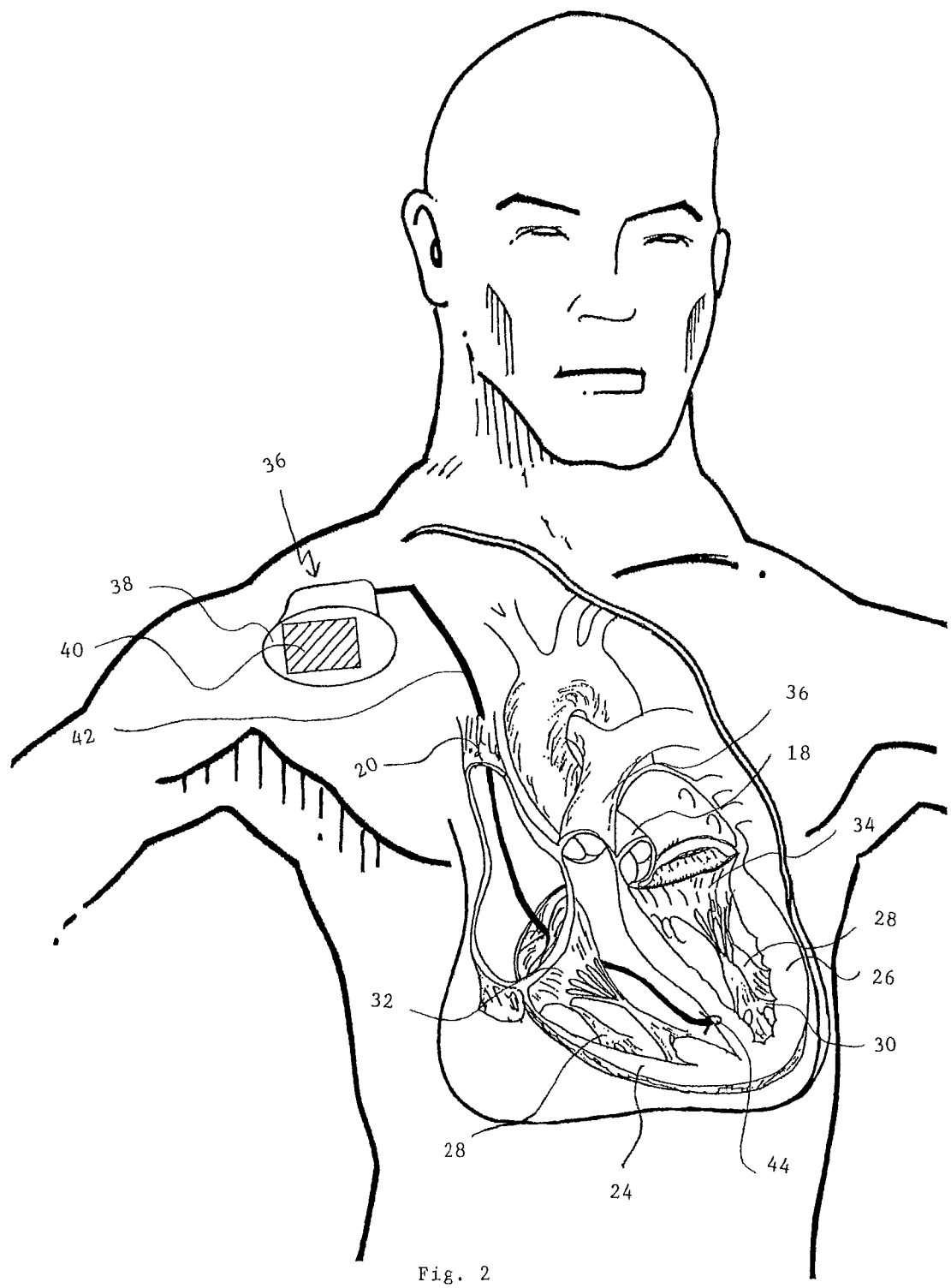
FIG. 2 is a schematic illustration showing a pacemaker or prior art monitoring device 36 like a HeartPod from Savacor Inc., a Chronicle system from Medtronics or a Pacemaker implanted at a patients shoulder area, remote from the heart. A lead for transportation of electrons runs from the implant can to the pressure transducer and back or in the case of a pacemaker to the heart tissue where the electron transfer takes place from the lead tip. These devices have a battery in the can.

The following description focuses on embodiments of the present invention applicable to a device, and in particular to a method of using said device, for transforming kinetic energy of a heart 1 into electrical energy. The device may transmit data outside the body. However, it will be appreciated that the invention is not limited to this application but may be applied to many other embodiments.

It will be understood that the Figures are merely schematic and are not drawn to scale. For clarity of illustration, certain dimensions may have been exaggerated while other dimensions may have been reduced. Also, where appropriate, the same reference numerals and letters are used throughout the Figures to indicate the same parts and dimensions.

In one embodiment the device according to the present invention is an intra cardiac device for heart function intervention. This device has the capability to transform kinetic energy obtained from heart muscle movement into electrical energy in use. This electrical energy may then be used to obtain information in respect of heart function.

The term "intervention" is, in this context, meant to be interpreted as monitoring, modifying, surveying, and/or controlling heart function and action.

In one embodiment of the present invention the herein presented device is designed to be implanted totally in the heart itself. Since the heart is constantly moving vigorously in all three dimensions, a device provided in the heart has a certain potential kinetic energy. With modern technology, e.g. micro mechanical systems, such kinetic energy may be detected and transformed into electrical energy. Since the heart never stops, it is not necessary to save any energy in batteries, if necessary possibly only momentarily in a capacitor. The electrical drain of 25 microamperes according to the prior art mentioned above includes the energy loss in the lead, thus the energy needed in a leadless system is much lower than that with a lead.

Modern technology permits new solutions for transforming kinetic energy into electrical energy by means of Micro Electro Mechanical Systems, also called MEMS. These new solutions may be implemented in respect of the embodiments according to the present invention. There are different methods to transform kinetic energy into electrical energy, by using an energy conversion unit 5.

Electrical energy may be obtained by means of unit 5 by inductive conversion from kinetic energy. In this case, a magnet 52 is moving relative a coil 50, whereupon a voltage and current is generated in the coil 50. Magnet 52 for instance may be connected via a connection means such as a rod 48 and a gearbox to a pendulum 46 for converting heart tissue movements in three dimensions to a suitable movement of the magnet 52 relative coil 50. This may be achieved by moving a magnet 52 back and forth through the coil 50, as suggested by Lee et al 2003, in "AA Size micro Resonators". Lee demonstrated that up to 830 microwatts could be achieved with such a conversion device.

Therefore, in one embodiment of the present invention, electrical energy is achieved by moving a magnet 52 back and forth relative a coil 50.

Another energy conversion solution is to transform movements of a magnetic pendulum 46 in another embodiment of energy conversion unit 5 into rotation and then have the magnet 52 to rotate in the coil 50. The Seiko watch, a self winding electric watch, is an example that may produce up to 1 mW. A spring like in a self winding wrist-watch and a gear system might accelerate the rotational speed to 15000 rev/min, an optimal rate. Kula and Najafi could achieve 2.5 microwatt at 10 Hz in a MEMS. Hence, a pendulum of 2 g is sufficient to convert enough energy to supply a pacemaker, such as a pacemaker unit 70. In this respect, one embodiment of the present invention transforms movements of a magnetic pendulum 46 into rotation, and then have the magnet to rotate in a coil 50 to obtain electrical energy.

Piezo-electrical materials may produce an electrical current with no mechanical parts moving. Pressure on a piezo-electrical material produces a voltage. Roundy, 2003, produced 0.2 mW on a 1 cm cube @ 120 Hz. Capacitive or electrostatic methods might also be used. The housing of the intra cardiac device may comprise piezo electric elements for the energy conversion. However, in this case a part of the housing area is blocked for other use, e.g. as electrode surface. As the intra cardiac device is very compact, housing surface is rather limited. Moreover, the housing itself has to be exposed to a pressure from the moving heart tissue. When the device is attached to the tissue, this is difficult to implement. Therefore, it is proposed to have a piezo electric conversion means inside the housing, which is exposed to a mechanical pressure when the heart tissue accelerates. For instance, a T-bar like element which generates a lever on a piezo electric element due to resulting inertia of a lever perpendicularly arranged to the piezo element may be used for piezo electric energy conversion. Accordingly, some embodiments of the invention are implemented by using piezo-electrical, capacitive or electrostatic energy conversion methods in embodiments of energy conversion unit 5.

Hence, a self-contained implantable intra cardiac device may be provided according to some embodiments.

Figure 3:
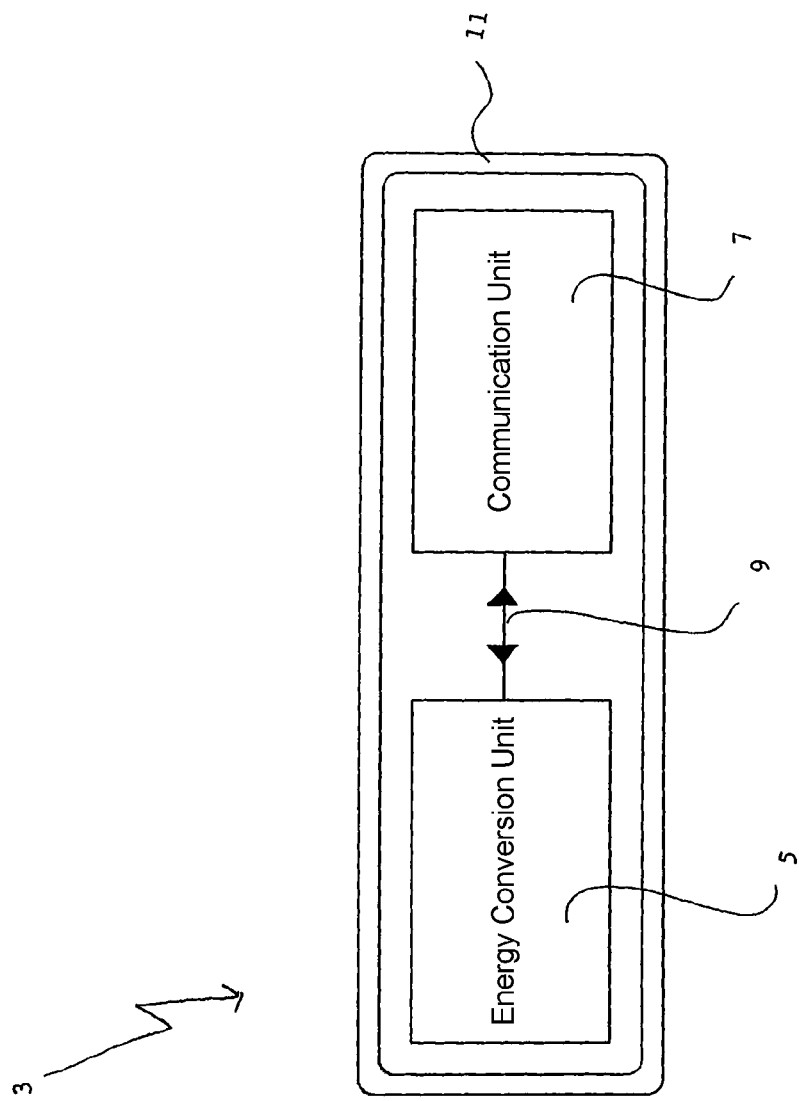
FIG. 3 is a schematic block diagram showing an intra cardiac device according to an embodiment of the present invention, wherein the device is capable of communicating with an external communication unit, e.g. outside the patient, via an integrated communication unit.
Figure 5B:
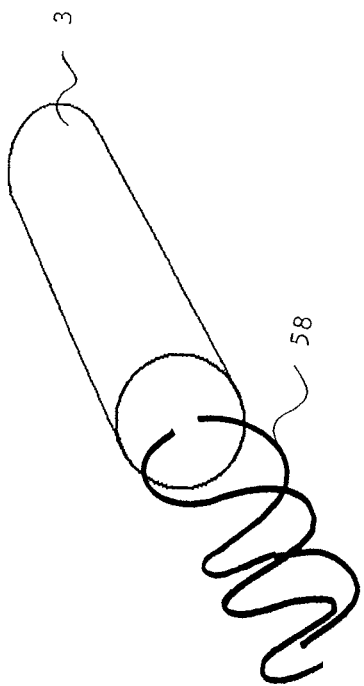
FIG. 5 *a*) is a schematic illustration showing tines as fixation means for an intra cardiac device.
Figure 5A:
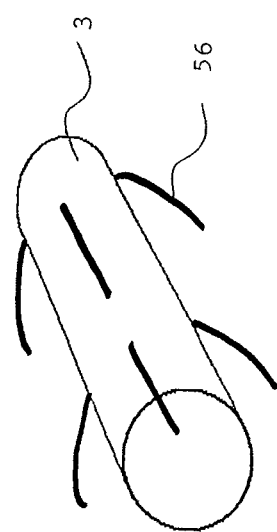
Figure 5C:
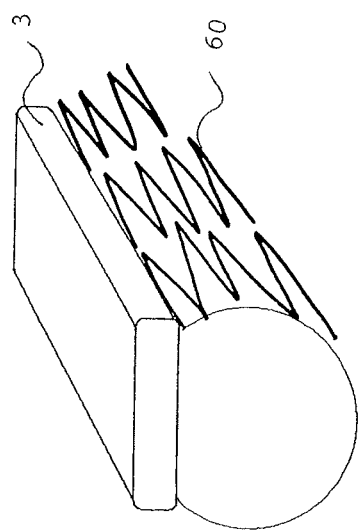
Figure 6A:
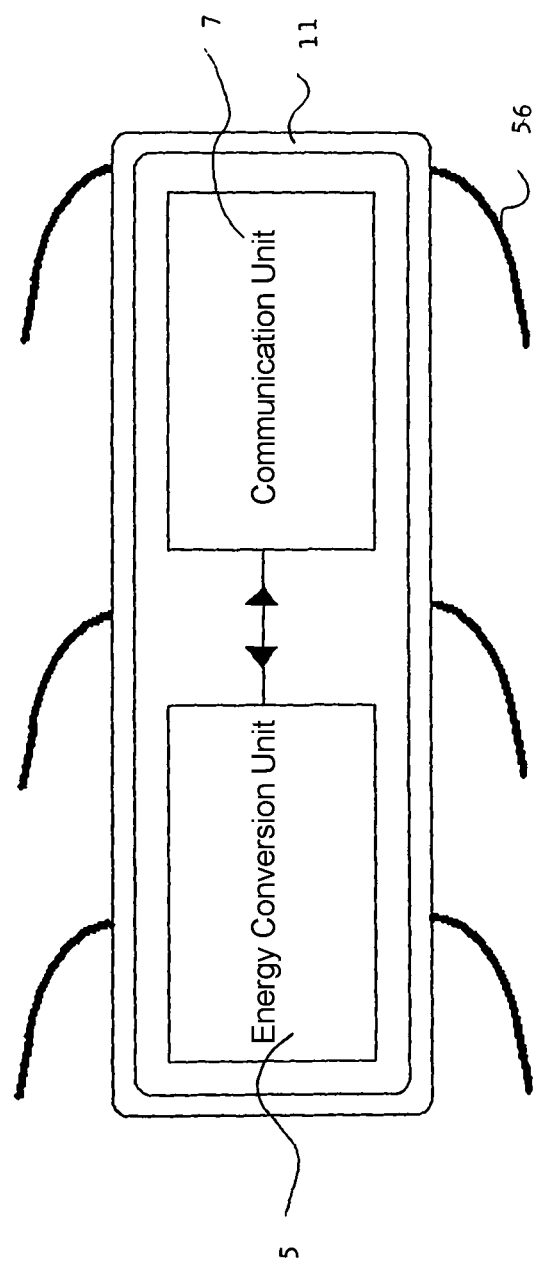
FIG. 6 *a*) is a schematic illustration showing an intra cardiac device according to an embodiment of the invention implemented with fixation tines.
Figure 6B:
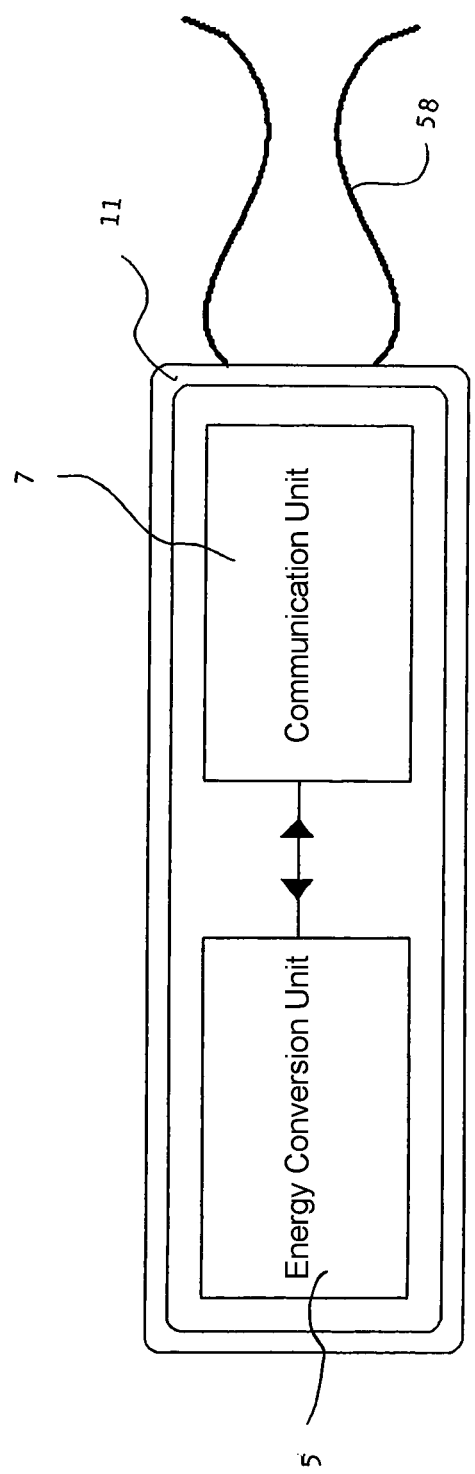

The device according to some embodiments of the present invention provides the possibility to continuously monitor the heart function and initiate early intervention, if the heart condition of a patient is deteriorating. An energy device fully implantable monitors in use the kinetic energy of a heart 1 and continuously transmit a report of the condition of the heart 1 to a receiver outside the body or to another device inside the body, for instance a pacemaker, such as a pacemaker unit 70, a defibrillator or an infusion pump able to adjust the amount of diuretics to be injected. For this purpose, energy conversion unit 5 is via communication element 9, e.g. by wires or wirelessly, connected to a communication unit 7 inside a housing 11 of the intra cardiac device 3, as shown in FIG. 3.

According to a specific embodiment, the device is self-contained and does not communicate with an extracorporeal device. The device according to this embodiment continuously monitors the heart function and initiate early intervention, if the heart condition of a patient is deteriorating. The device is in use fully implanted in the heart 1 and converts kinetic energy from heart movements into electric energy. The conversion signal provides information to monitor the kinetic energy of the heart 1 and continuously analyzes this information in order to activate a pacing circuitry if required.

A device according to one embodiment of the present invention may also be used in acute situations in the intensive care unit for patients suffering from acute heart failure, for instance after large myocardial infarctions, after catheter based coronary artery intervention or after cardiac surgery. By means of the device according to the embodiment of the present invention, the kinetic energy of the heart 1 is transformed into electricity; the amount of electrical energy achieved is related to the force of movement of the heart 1, an indicator of the heart condition. More specifically, an electrical signal is obtained when converting the heart movement kinetic energy into electrical energy. The electrical signal has a characteristic electrical voltage and current over time. For instance, the maximum amplitude of the electrical signal may deliver information how fast the heart 1 is accelerating. The curve form may give information how the muscle exactly is accelerating, etc. Furthermore, no energy is transferred to the herein presented inventive device from outside the heart 1.

In respect of the PM's according to the prior art, the herein presented device, according to some embodiments of the present invention, eliminates among others the problems related to batteries and leads, since there is no battery and there are no leads comprised in the herein presented PM.

In a first embodiment an energy unit is utilizing induction for creating electricity electromagnetic, by transforming the kinetic energy of the heart movements. This is achieved either by moving a magnet back and forth relative a coil 50, e.g. through the coil 50, or by rotating a magnet 52 relative a coil 50, e.g. by rotating a magnet 52 in a coil 50 or by rotating a coil 50 around a magnet 52, e.g. by means of a pendulum effect.

In a second embodiment electric current unit is utilizing a piezo-electric material, i.e. a material that creates an electric current when deformed.

In still another embodiment an energy unit is created utilizing electrostatic or capacitive technology.

The amount of electricity produced is an indicator of the kinetic energy of the heart 1 reflecting acceleration and movement of the site where the device is implanted. Acceleration and movements are indicators of the heart muscle condition at a given time. According to some embodiments, the device has a transmitter emitting a signal to a receiver, e.g. outside the body. Thus, the device according to some embodiments comprises an energy unit, an electronic control unit, a transmitting unit and fixation means. Some embodiments of the device may also comprise a transmitting and receiving unit (also called transceiver unit) instead of only a transmitting unit.

The receiver may also be incorporated in another device according to another embodiment of the invention. Thus, one implanted device may communicate with another implanted device, e.g. to give the other implanted device instructions in respect of when and how to act. For instance, a first implanted device may convert kinetic energy, analyze heart condition, and send a signal to a second implanted device if a heart failure is detected. The second device also converts kinetic energy for powering a receiver and a pacing circuit. When the second implanted device receives a signal from the first implanted device, e.g. that pacing is necessary, the second implanted device takes appropriate action.

In one embodiment wireless communication is provided by means of radio frequency (RF) transmission which may be digitally coded.

In one embodiment the means of communication is provided by so called Bluetooth® technology.

ZigBee® technology might also be used in other embodiments. ZigBee® is a published specification set of high level communication protocols designed to use small, low power digital radios based on the IEEE 802.15.4 standard for wireless personal area networks (WPANs). The technology is designed to be simpler and cheaper than other WPANs such as Bluetooth®. The most capable ZigBee® node type is said to require only about 10% of the software of a typical Bluetooth® or Wireless Internet node, while the simplest nodes are about 2%. ZigBee® provides an inexpensive self-organizing mesh network. However, it has not yet been envisaged for use in implanted medical devices. ZigBee® is designed to use very small amounts of power. This makes ZigBee® perfectly suited for use in the implantable cardiac devices of the present invention.

In still another embodiment ultrasound may be used for wireless communication with the intra cardiac device(s).

The data retrieved outside may be exact numeric data of a current status or may also only comprise trends.

Figure 8:
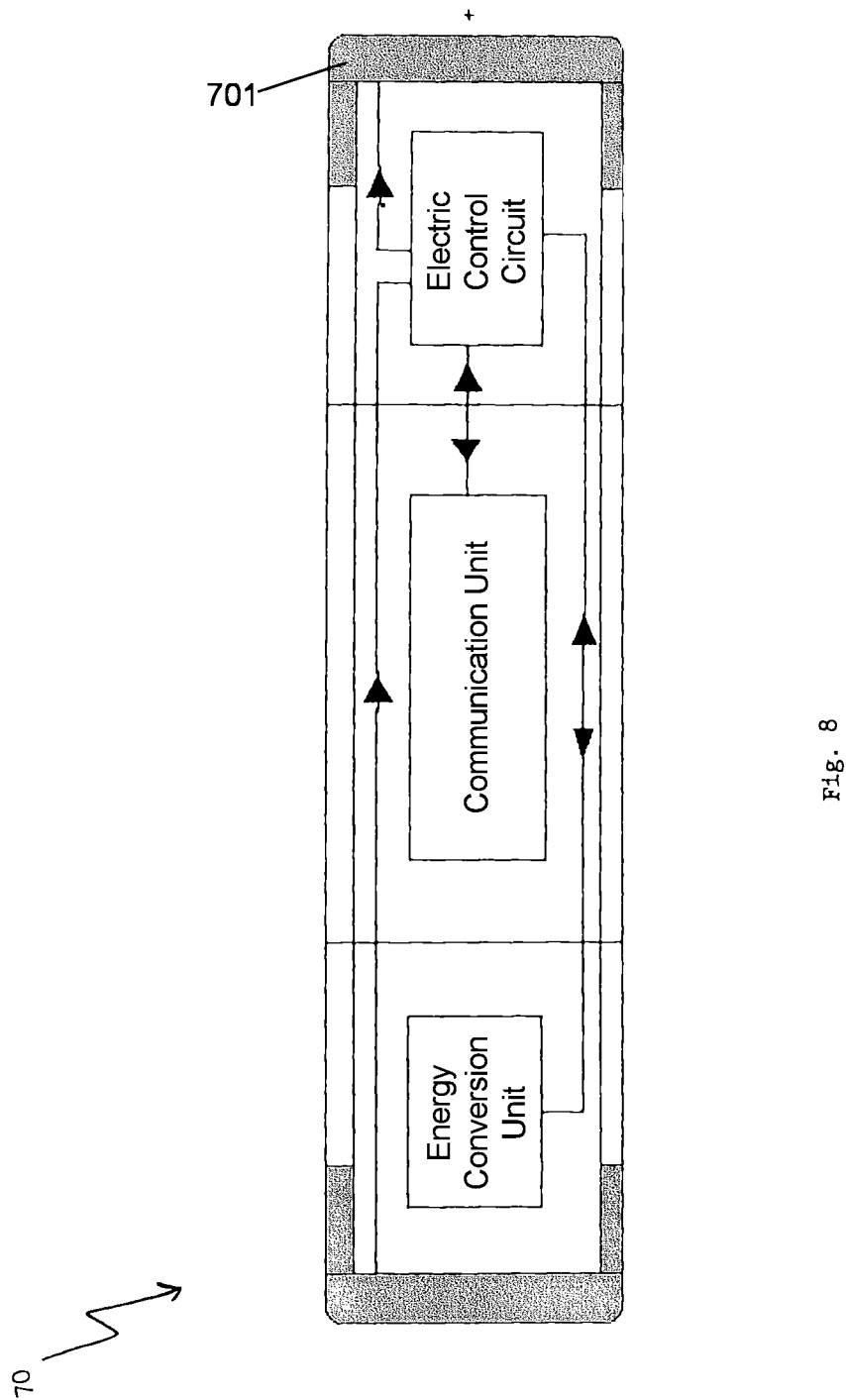
FIG. 8 is a schematic block diagram of showing an intra cardiac device according to an embodiment of the invention having an energy unit powering a cardiac stimulator in the form of a pacemaker.
Figure 9:
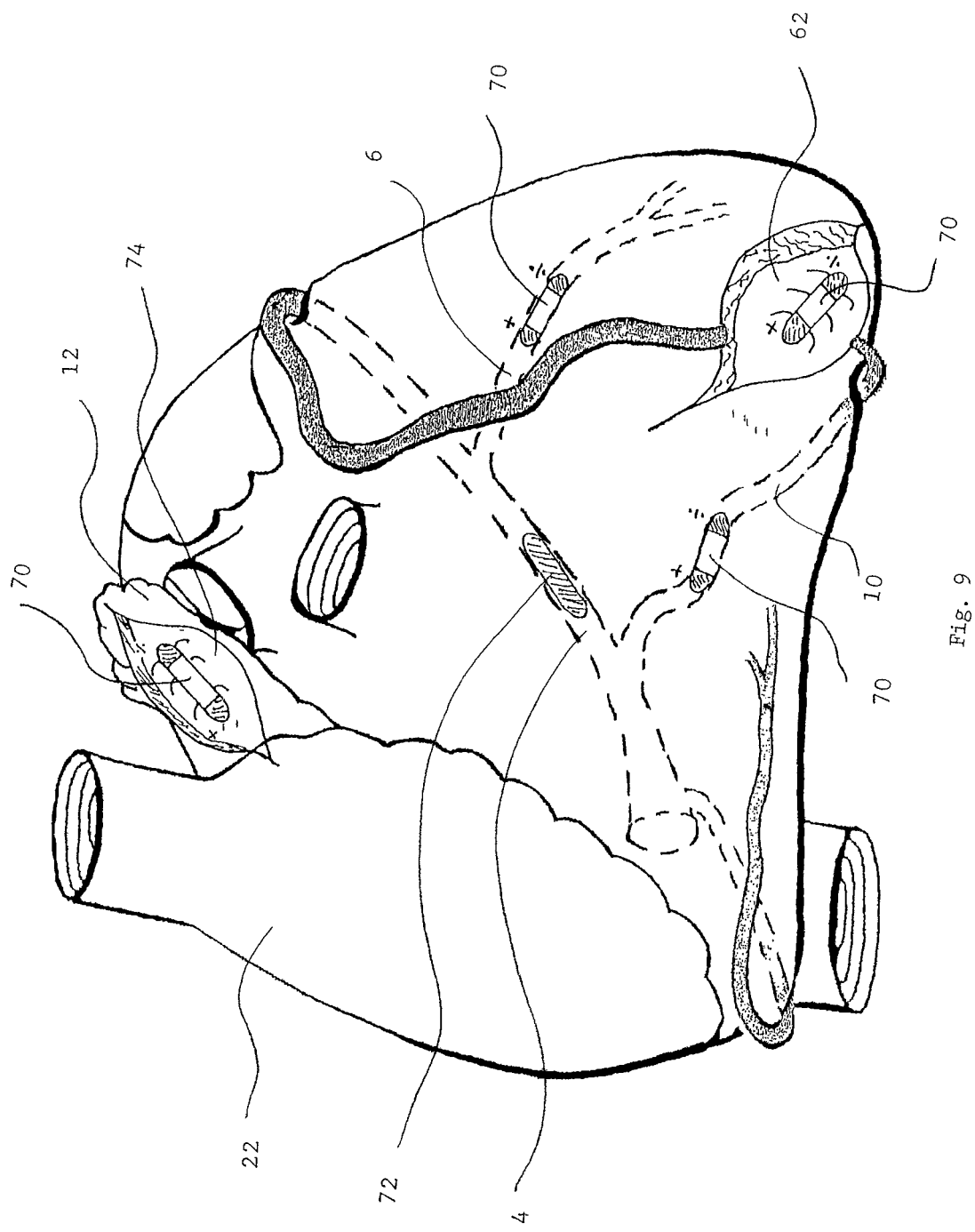
FIG. 9 is a schematic illustration showing a complete pacemaker system implemented with four intra cardiac device according to embodiments of the invention implemented as pacemaker units are implanted in the lateral marginal vein, the middle cardiac vein, in the right ventricle and in the right atrium appendage, respectively, and a further intra cardiac device according to an embodiment of the invention implemented as a defibrillation unit is located in the great cardiac vein, wherein the devices may communicate with each other and outside the patient by means of the built in communication units.
Figure 10A:
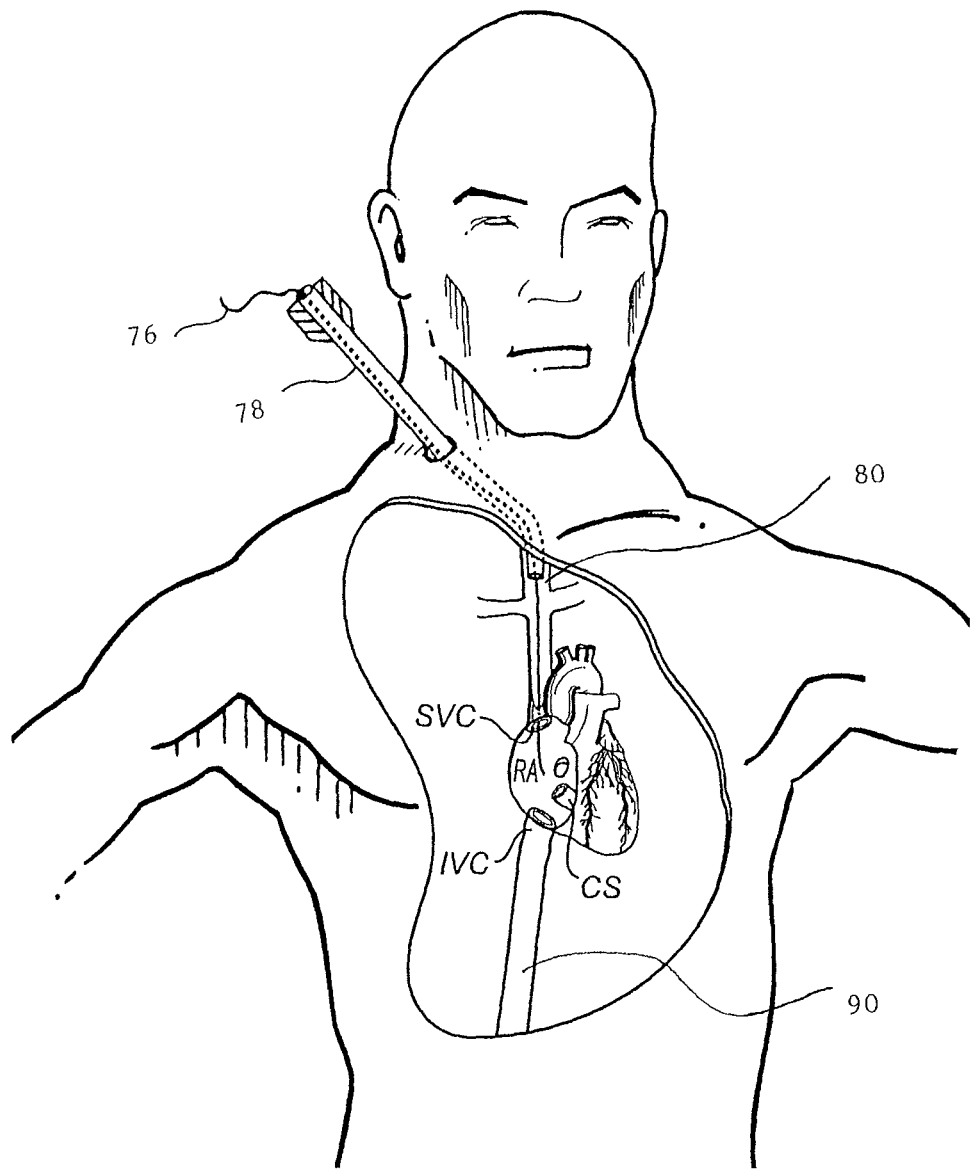
FIG. 10 *a*) is a schematic illustration showing access to the vein system through the internal Jugular vein.
Figure 10B:
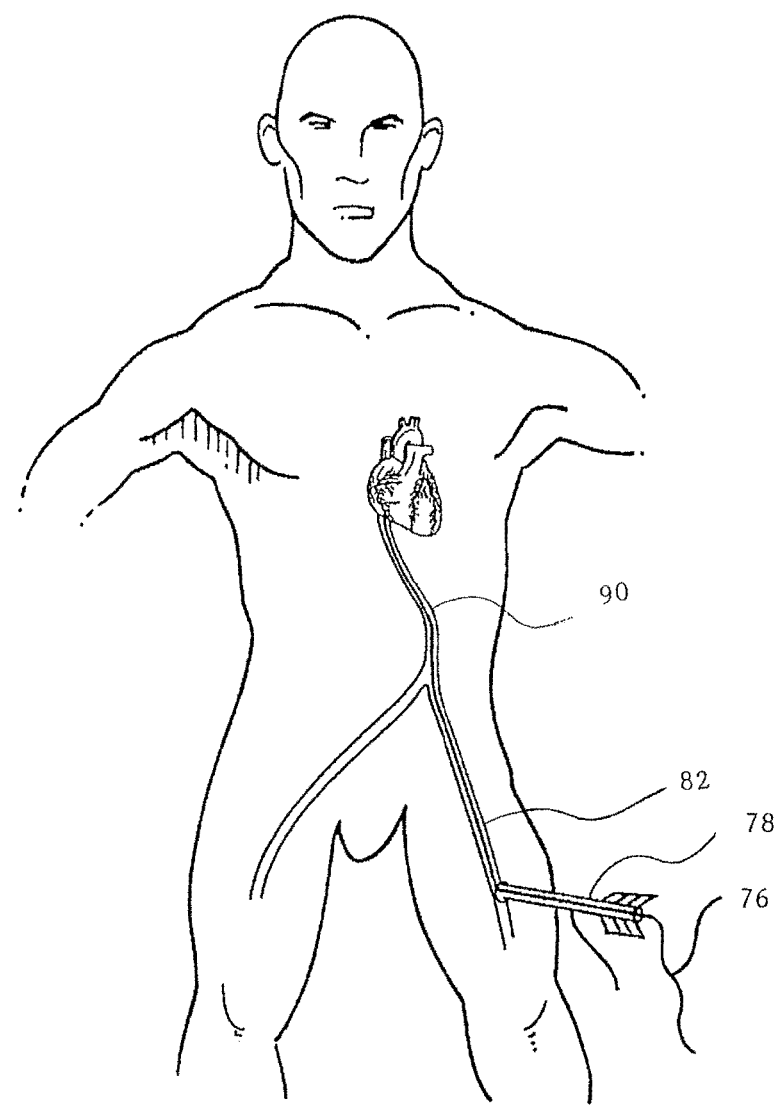
Figure 10C:
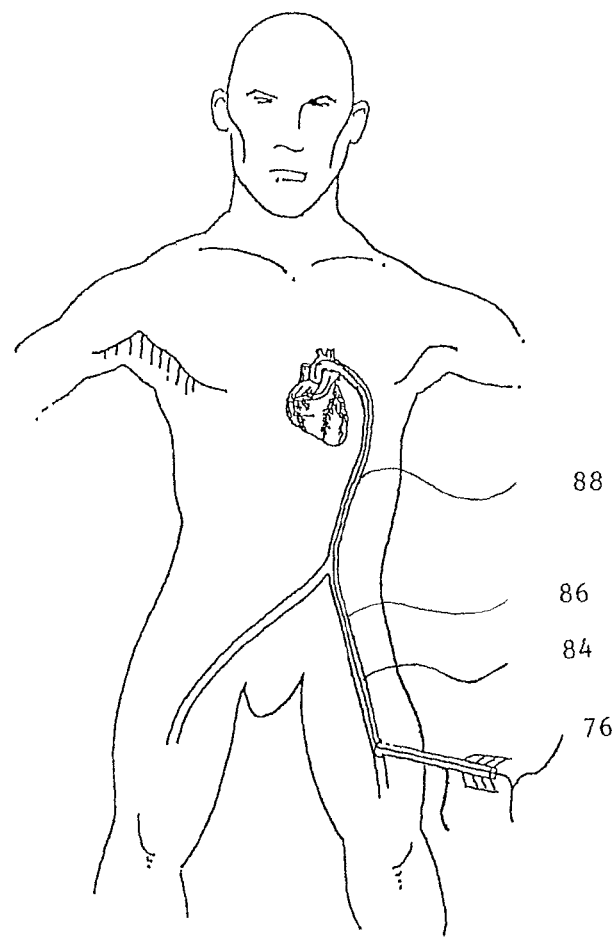
Figure 11:
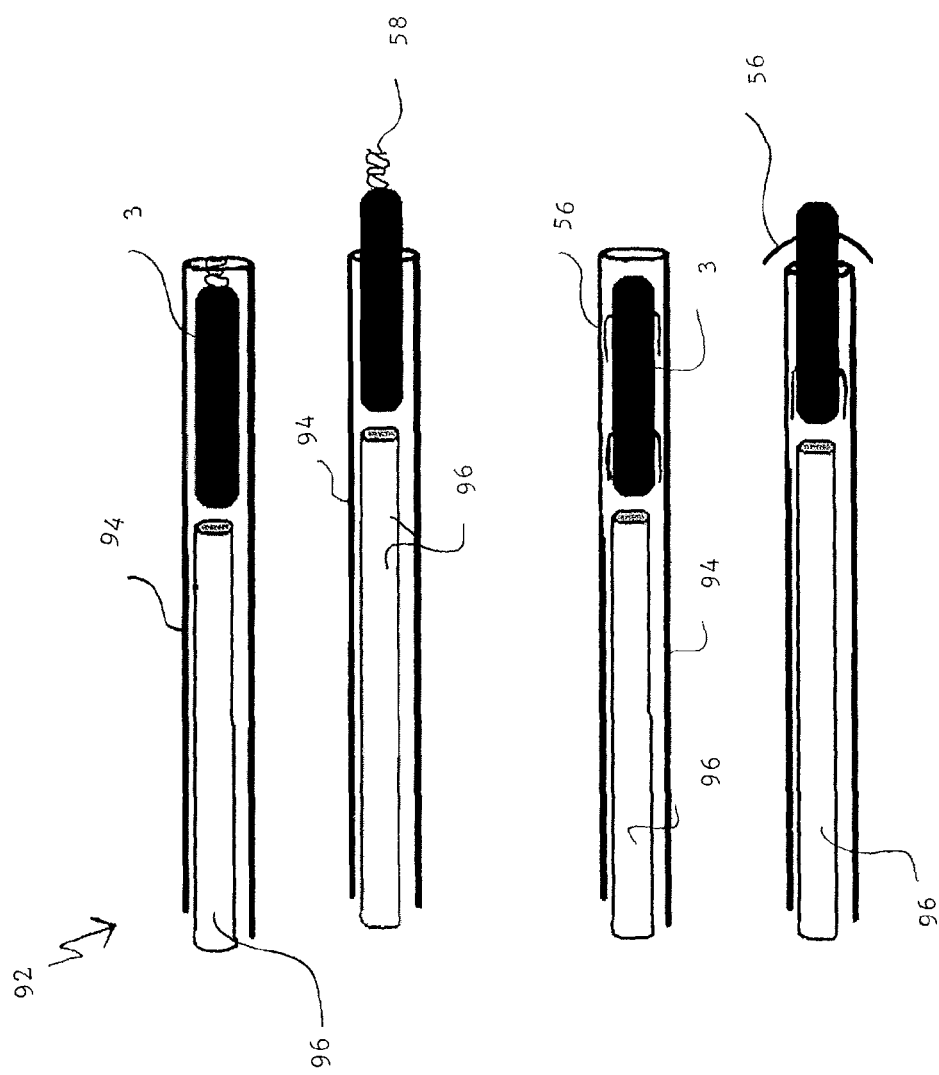
FIG. 11 is are schematic illustrations showing a delivery system for fixation with tines and a screw respectively.
Figure 12:
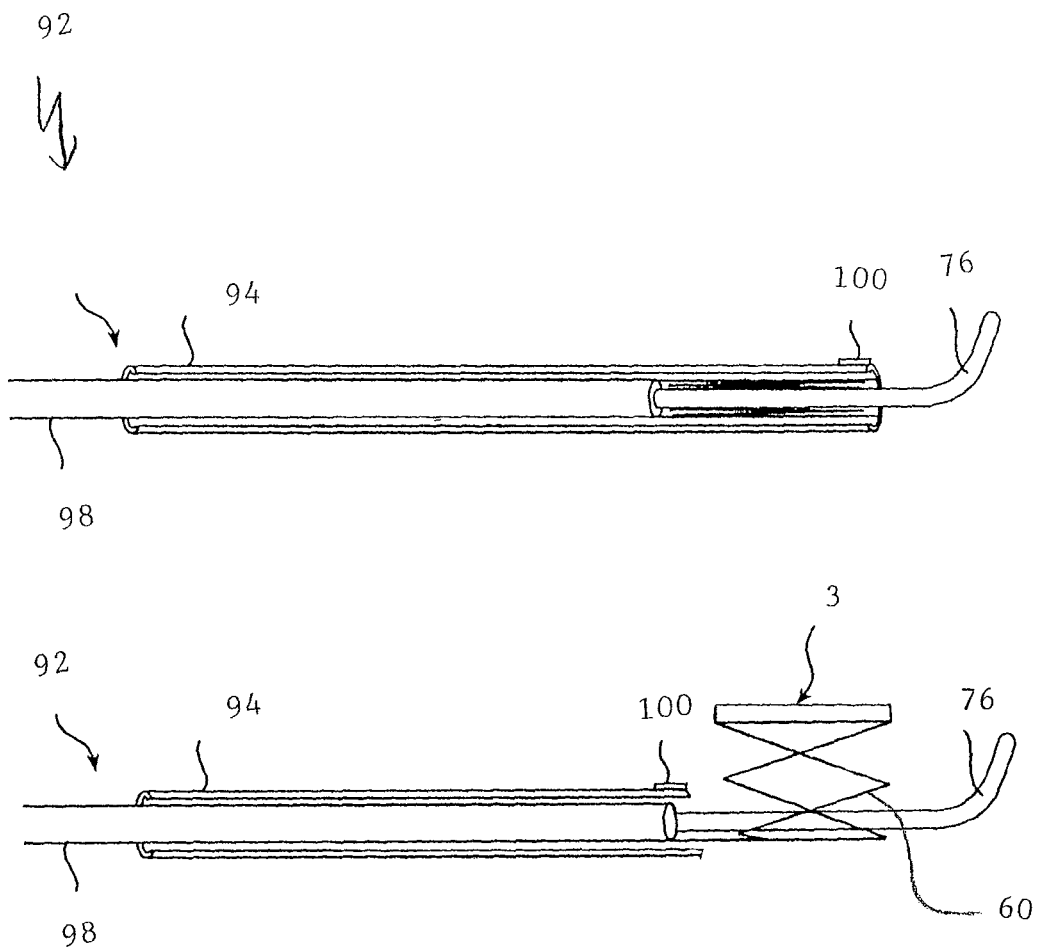
FIG. 12 is a schematic illustration showing a delivery system for fixation with stent.
Figure 13:
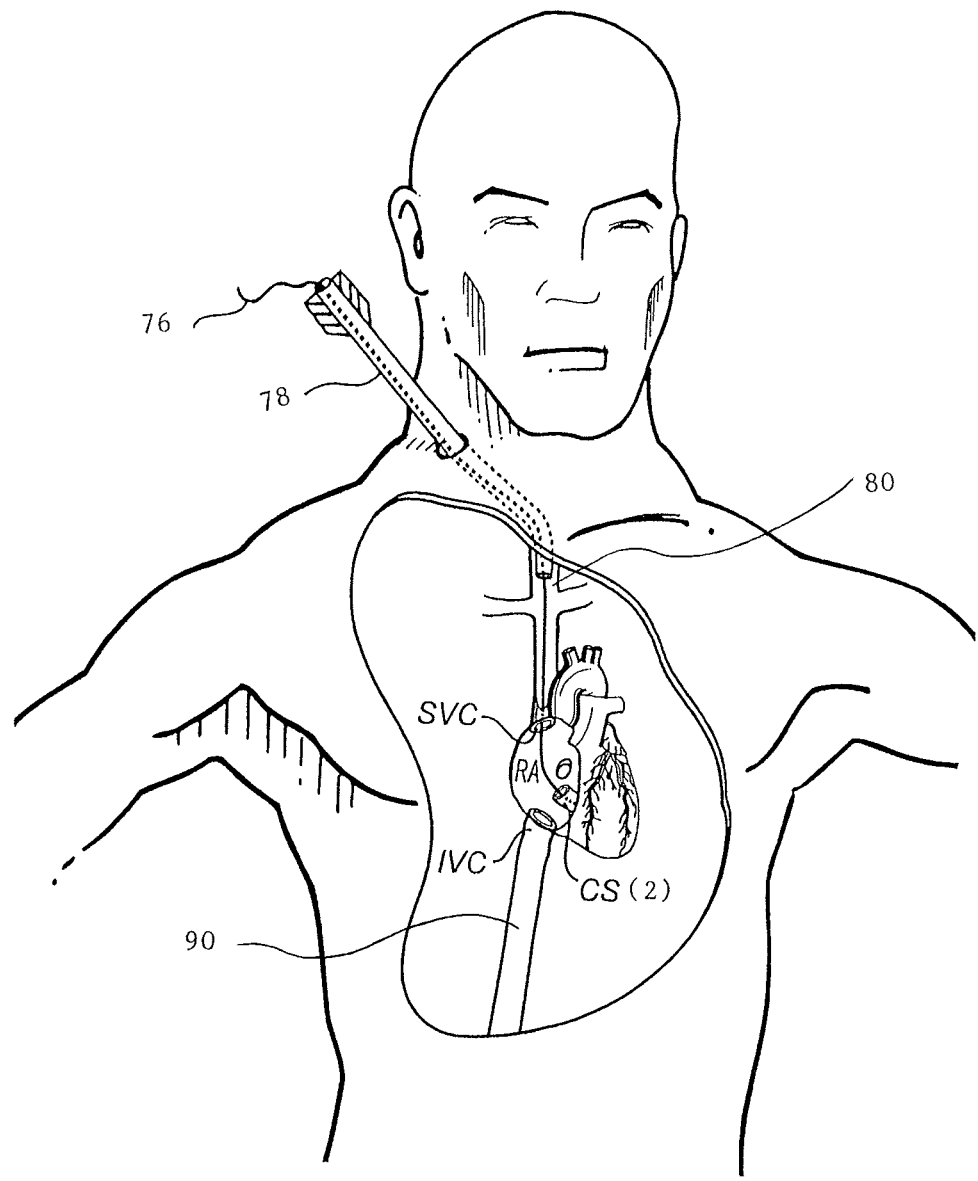
FIG. 13 is a schematic illustration showing the insertion of a guide wire into the coronary sinus through the internal Jugular vein.
Figure 14A:
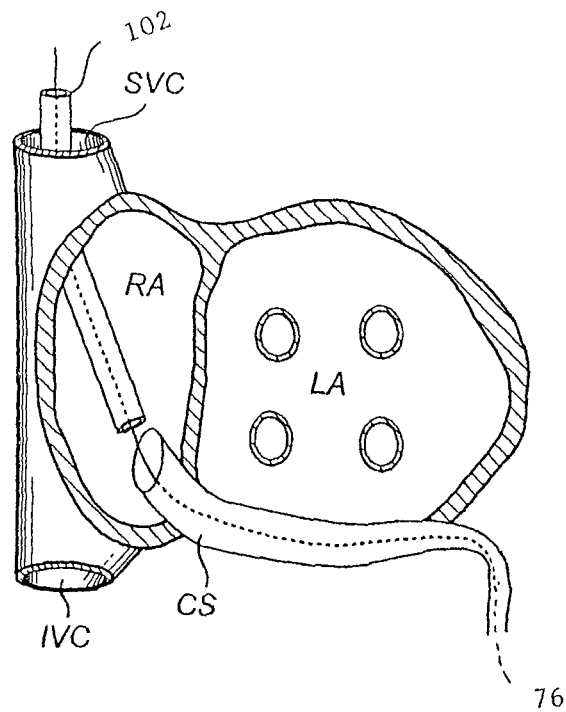
FIG. 14 *a*) is a schematic illustration showing a guide wire and a guiding catheter introduced through the coronary sinus, the great cardiac vein and into the anterior inter-ventricular vein.
Figure 14B:
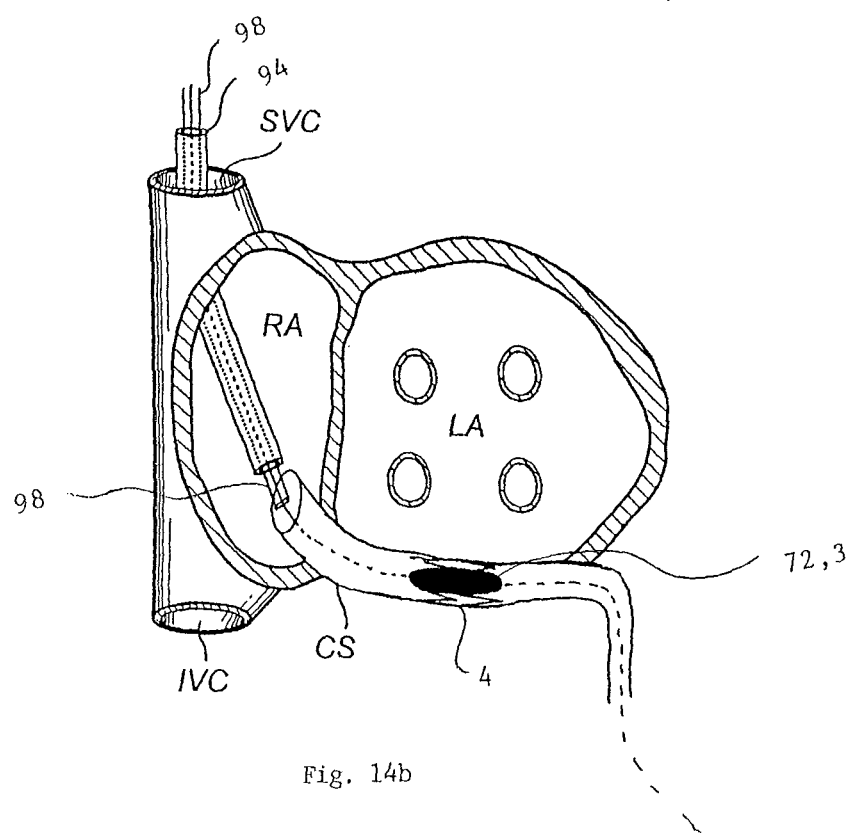
Figure 15:
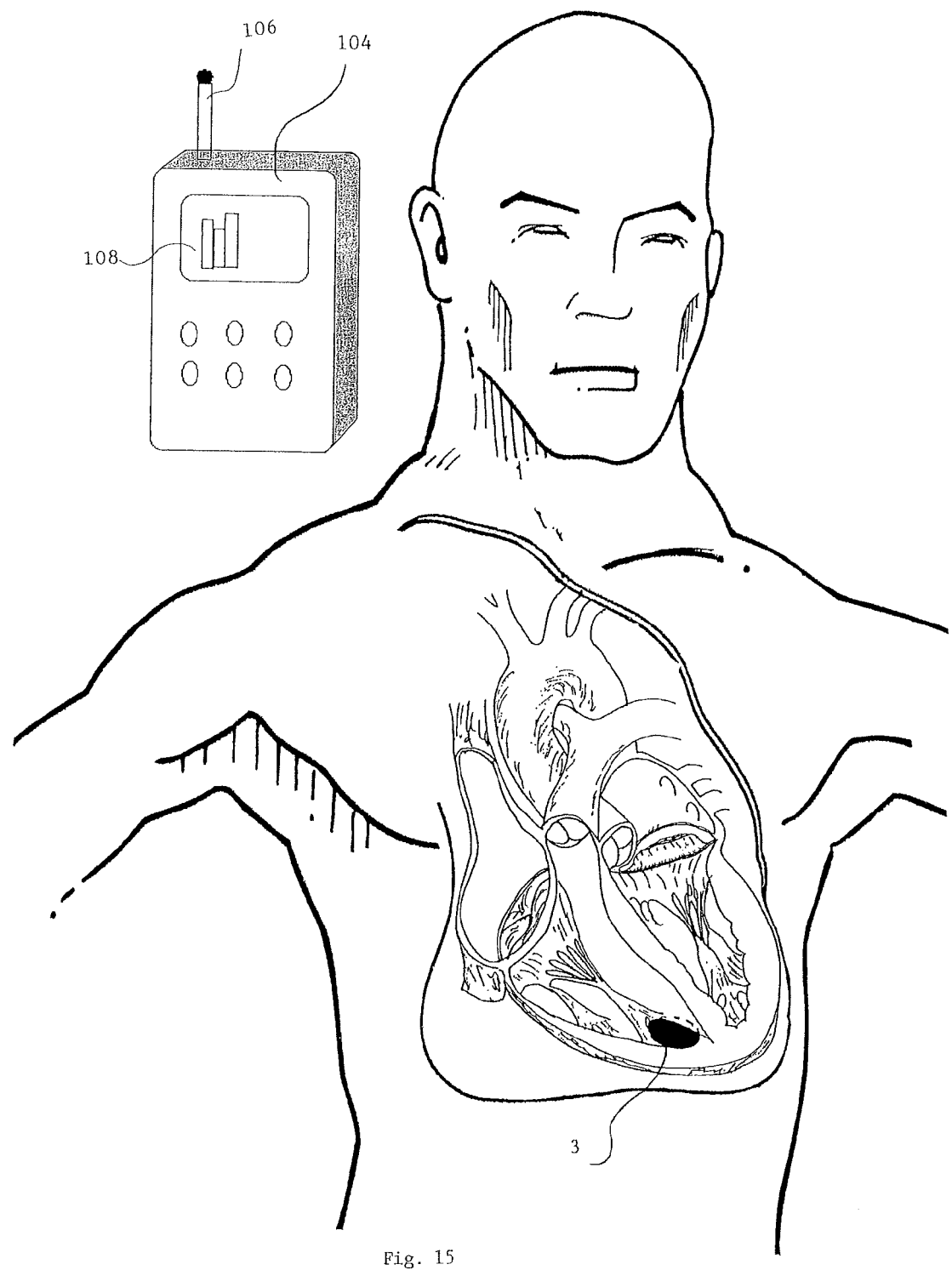
FIG. 15 is a schematic illustration showing a complete heart function monitoring system according to an embodiment of the invention with an external communication unit.

In another embodiment a device and a method for treatment of heart blocks and arrhythmias by means of an electrical cardiac stimulator without battery and leads are presented. The device (FIG. 8) is designed to be completely implanted in a heart 1 or on a heart surface. In this embodiment the device comprises five main components: an energy conversion unit 5, an electronic control circuit 700, an electrode contact surface 701 towards the heart tissue, a communication unit 7 and finally means for attachment or fixation in or to the heart 1.

In one embodiment of the intra cardiac device according to the present invention in the form of an electrical cardiac stimulator, an energy unit is utilizing induction for creating electricity by means of electromagnetically converting kinetic energy from heart movement into electrical energy. This is achieved either by moving a magnet 52 back and forth relative a coil 50 or by rotating a magnet 52 relative a coil 50, e.g. by rotating a magnet 52 in a coil 50 or by rotating a coil 50 around a magnet 52, e.g. by means of a pendulum effect.

In another embodiment of the electrical cardiac stimulator according to the present invention, an energy conversion unit is utilizing piezo-electric material, a material that creates an electric current when deformed.

In still another embodiment of the electrical cardiac stimulator according to an embodiment of the present invention, an energy conversion unit is based on electrostatic or capacitive conversion technology.

According to one embodiment, the electrical cardiac stimulator's electronic circuit utilizes traditional PM algorithms on an electronic chip. The chip may for instance be of rectangular or square surface area, and by estimation the complete area is with current technology less than approximately one square centimeter in size. Further miniaturization is envisaged with emerging technologies. The device has two electrode contact surfaces, preferably one at each end of the implant, one positive pole receiving the electrons and one negative emitting electrons into the heart tissue. The electrode contact surfaces are made of good electrically conducting metal material like copper or steel or other alloys. They may be covered with porous material like activated carbon, sintered platinum-iridium or sputtered titanium-nitride. The current is concentrated in a small area of contact with the myocytes by means of designing the geometrical surface area of contact of the electrodes as small as is optimal. The surface may also be eluting steroids like dexamethasone from the surface initially in order to limit inflammation during healing in. The electrical cardiac stimulator device has a unit of communication. The communication unit 7 may communicate with communication units in other devices implanted in the same heart 1, e.g. one in an atrium and one in a ventricle, or one electrical cardiac stimulator in the implementation of a PM unit and one electrical cardiac stimulator in the implementation of an ICD unit. Thus, one unit may serve as a master and the others are slaved to the master. Thus, one device may communicate with another device, e.g. to give the other device instructions in respect of when and how to act. The communication unit 7 may also be designed to communicate outside of the patient. Communication may occur one-way out of the device in order to deliver information from the implanted device (in this case the device has a transmitter only), or two-way so that the implanted device also may receive information (in this case the device has a transceiver). In either case information that is transmitted may comprise information related to follow up of the device's function and for adjustments of it's mode of operation, for instance administrative data, programmed data like mode, rate etc., measured data like heart rate, mechanical cardiac function values, like local acceleration at the implanted devices location, or the electrical pulse rate, electrical pulse amplitude, power unit condition etc., or stored data. The means of communication is based on wireless transmission technologies. In one embodiment the means of communication is by means of radio frequency (RF) waves. Communication may be digitally coded and/or authenticated in order to provide a secure and reliable data transmission to and/or from implanted device(s).

In another embodiment of the electrical cardiac stimulator device according to the present invention the means of communication is based on so called Bluetooth® technology. The new ZigBee® technology may also be used in respect of the presently described electrical cardiac stimulators.

In still another embodiment of the electrical cardiac stimulator device according to the present invention ultrasound transmissions through the body may be used for wireless communication to/from the implanted device(s).

Again Nanotechnology and MEMS may be utilized for minimizing the communication unit 7 in the device.

In yet another embodiment the intra cardiac device according to the present invention is a congestive heart failure monitoring device 3. The congestive heart failure monitoring device 3 is intended to be inserted and fixated adjacent to the left ventricle of the heart 1. Preferably the device is inserted in the vein system through the coronary sinus 2 and the great cardiac vein 4 into smaller branches along the lateral wall of the left ventricular wall 26. Other positions in the vein system are in the anterior inter-ventricular vein on the front of the heart 1 or in the middle cardiac vein 10 behind the heart 1 between the left and the right ventricle, or in the great cardiac vein 4. In cases of right heart failure separately, the device is placed close to the right ventricle, in case only one embodied device is implanted.

In the Figures, e.g. FIG. 1, furthermore the following elements are illustrated for a better understanding of the present invention: anterior inter-ventricular vein 8, left atrium appendage 14, pulmonary artery 16, superior vena cava (SVC) 20, right ventricular wall 24, tricuspid valve 32, mitral valve 34, right atrium appendage cavity 74, the femoral artery 84, the iliac artery 86, the aorta 88 and the inferior vena cava (IVC) 90.

The positioning of electrical cardiac stimulator devices, such as pacemaker (PM) devices, for example a pacemaker unit 70, according to embodiments of the present invention may also be more diverse or distributed over the heart 1, depending on the function of the different components of a electrical cardiac stimulator system. For instance a first intra cardiac device implemented as a PM for stimulation of the right ventricle (RV) may be positioned inside the RV, in the middle cardiac vein 10 or in the coronary sinus 2. A second intra cardiac device implemented as PM for stimulation of the left ventricle (LV) may additionally be positioned inside the LV from the aorta 18, in the lateral marginal veins 6, in the great cardiac vein 4 or in the coronary sinus 2. A third intra cardiac device implemented as a PM for stimulation of the right atrium 22 may additionally be positioned inside the right atrium wall or right atrium appendage 12. An intra cardiac device implemented as a defibrillator may additionally be positioned inside the RV, the marginal veins, the great cardiac vein 4, the coronary sinus 2 or in the middle cardiac vein 10. Each of these intra cardiac devices implemented as a units will communicate with each other. For instance during open chest surgery, the devices are attached to the heart surface directly, a technique that optimizes positioning.

An embodiment of the method according to the present invention is now described. The method provides for monitoring of the heart function by means of converting kinetic energy from the heart 1 to electrical energy and using information related to the electrical energy, e.g. the amount of electricity produced over time, as an indicator of the heart function.

Initially access to the circulatory system is established. More precisely, one specific way is to first establish access to the vein system by means of puncturing a large vein with a needle, wherein such veins might be the cubital arm vein, the cephalic vein, the internal jugular vein 78, the subclavian vein, the femoral vein 82 or any other vein large enough. Subsequently, a guide wire 76 is inserted and an introducer sheath 78 with a hemostatic valve is placed over the wire. The guide wire 76 is then withdrawn. A diagnostic catheter 102 is inserted in the introducer sheath 78 to the location intended for positioning the device in the body. Preferably the catheter is inserted in the vein system through the coronary sinus 2 and the great cardiac vein 4 into smaller branches along the lateral wall of the left ventricular wall 26, the lateral marginal branches. Other suitable positions in the vein system are for instance in the anterior inter-ventricular vein on the front of the heart 1 or in the middle cardiac vein 10 behind the heart 1 between the left and the right ventricle. Once the diagnostic catheter 102 is in position an angiogram of the vein system is achieved using contrast dye. By interpreting the image from the angiogram of the vein, the proper position for the device is determined. A guide wire 76 is now advanced to the selected position in the vein and beyond, whereupon the diagnostic catheter 102 is withdrawn, leaving the guide wire 76 in position. Over the guide wire 76 a guiding catheter is advanced to the deployment site or adjacent. Now the delivery system 92 is advanced over the guide wire 76 but inside the guiding catheter to the desired site. If the device is kept inside the delivery system 92 by means of a restraining catheter, this is now retracted, thereby exposing the device that is expanding inside the vein, e.g. by a shape memory effect. This shape memory effect may for example be accomplished by polymers that present this feature, or with other suitable materials such as nitinol, which is a nickel-titanium alloy presenting this feature. The device may thus fixate itself at the selected position, or in case the device has tines 56 the tines 56 will attach into the vein wall, keeping the device strongly fixated. In case the device has a screw 58 for fixation in the tissue, the delivery system 92 is rotated in the proper direction until the screw 58 is solidly attached in the heart tissue. In case the fixation means is a stent 60 made of stainless steel, or another alloy, without shape memory, the fixation in the vessel is made by inflating a balloon inside the stent 60 for stent expansion. A pushing rod 96, a pushing catheter 98, and an X-ray marker 100 are further elements used for certain of the herein described procedures.

If the device is to be deployed in a cavity like the RV 62, LV 64 or the right atrium 22, the same actions as above are executed until the guiding catheter and the delivery system 92 is in position inside the cavity. The device is advanced and in case of a screw attachment the delivery system 92 is rotated in the proper direction until the device has a strong attachment in the heart tissue wall. In case the device has fixation tines 56 on the outside a place between the papillary muscles 28 or between the trabecles of the heart muscle 30 is located where the tines 56 get a good attachment and then the device is released from the delivery system 92 by retracting the delivery catheter 94 from over the device.

Figure 7A:
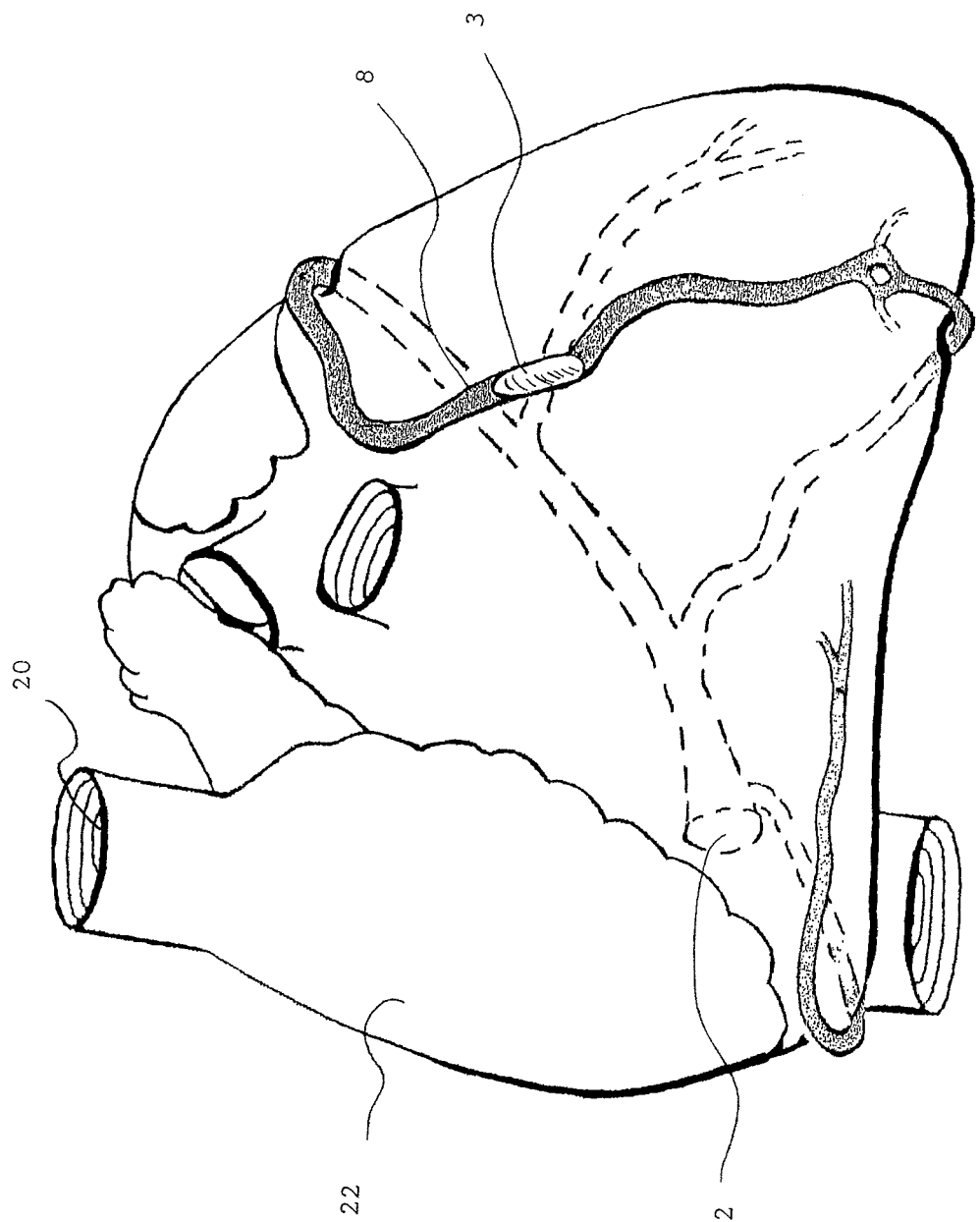
FIG. 7 *a*) is a schematic illustration showing an intra cardiac device according to an embodiment of the invention delivered and fixed in the anterior inter-ventricular vein.
Figure 7B:
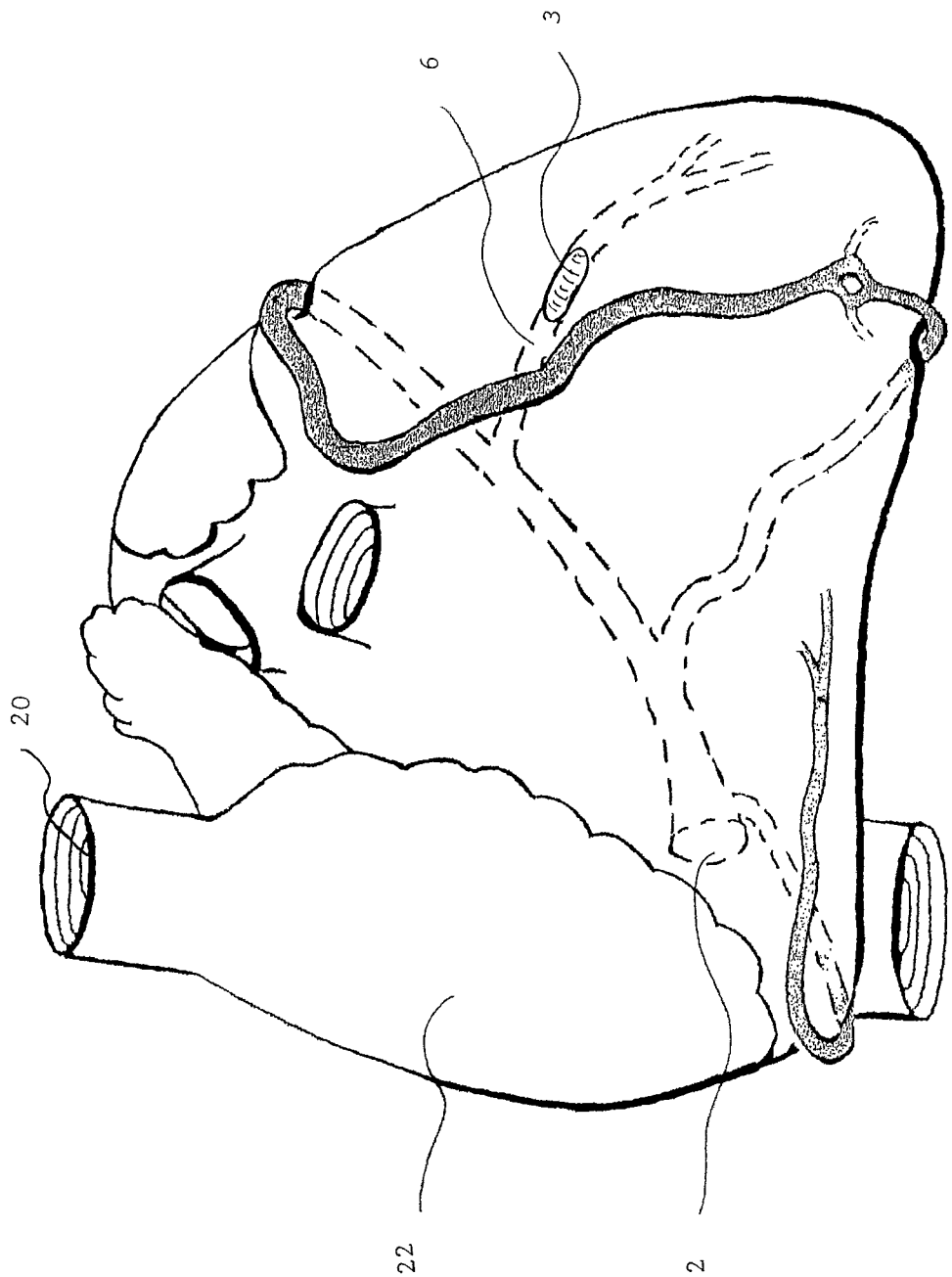
Figure 7C:
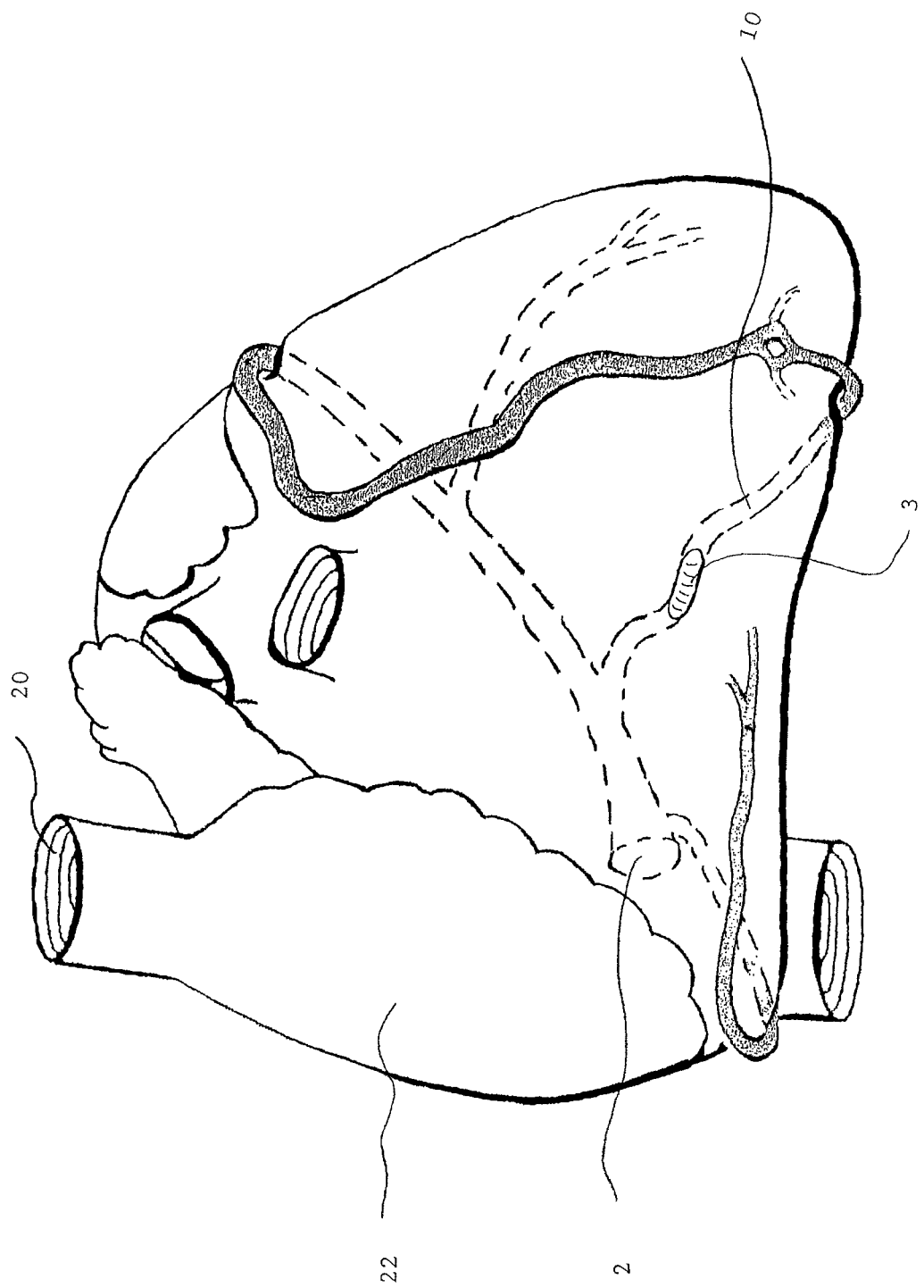
Figure 7D:
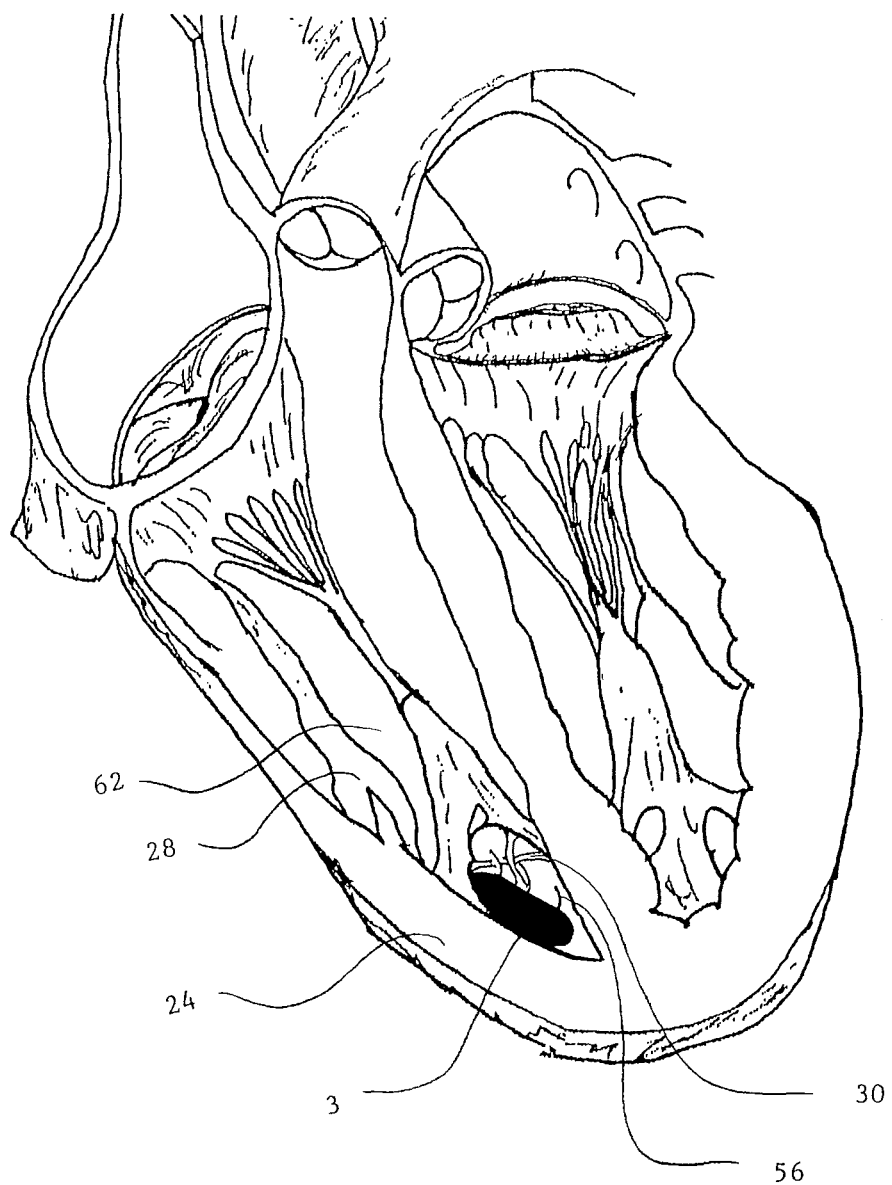
Figure 7E:
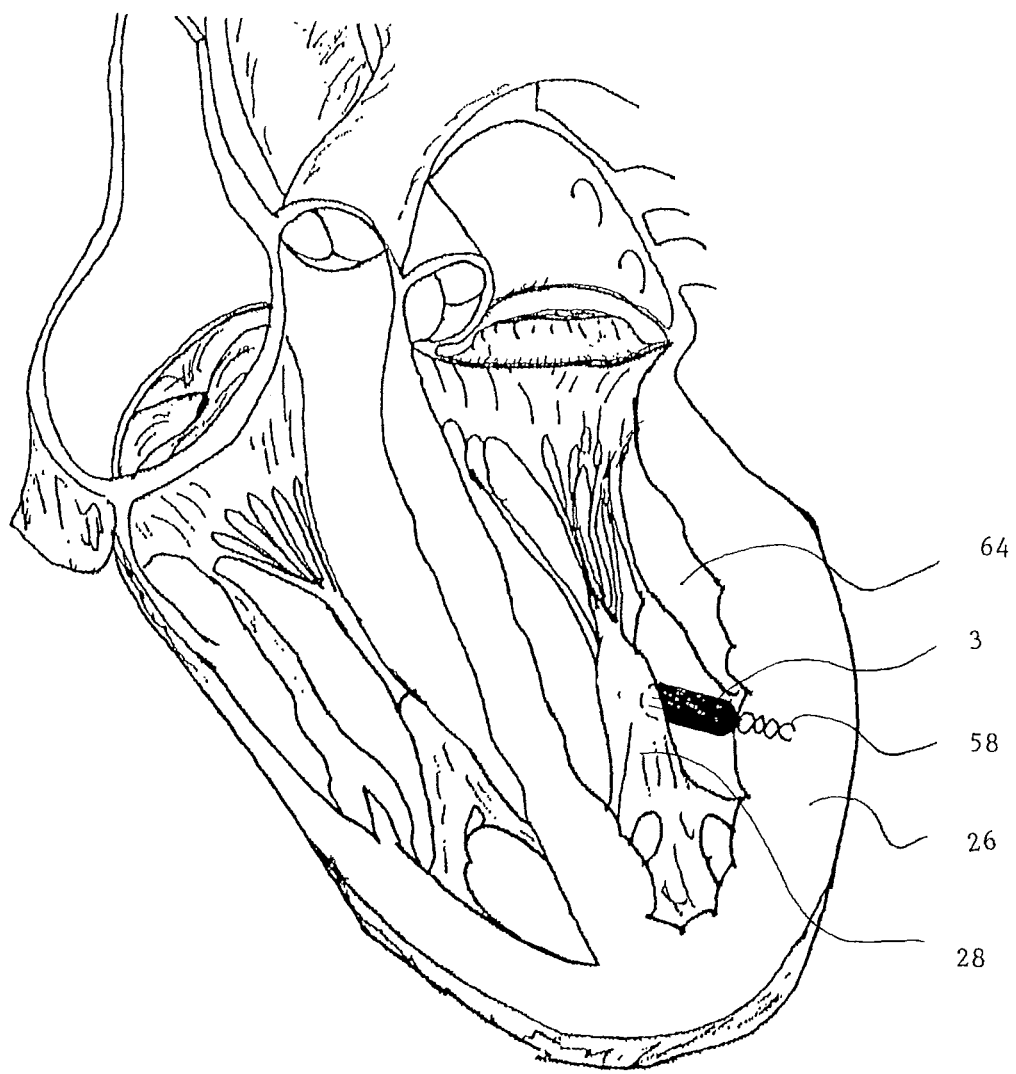
Figure 7F:

Other fixation means are for instance eyelets 66 or a suture 68, as shown in FIG. 7f.

Once the intra cardiac energy and monitoring device 3 is in the proper position the movements of the heart 1 produce a certain amount of electricity in the device. This is done by converting kinetic energy from the heart movement into electric energy, as described above.

The communication unit 7 of the intra cardiac device may transmit information to a receiver or an external communication unit 104, e.g. outside of the body or in other implanted intra-cardiac devices. The information may be used for interpretation of the current or previous heart condition. The external communication unit 104 may comprise an antenna 106, which may be integrated inside a housing of unit 104, and a display 108 for visualization of information.

The receiver outside of the body may be part of or connected to a mobile telephone or a fix-net telephone line for direct communication to a physician or a nurse for monitoring purposes and for taking the right actions. The receiver might also be a part of or connected to intensive care monitors. The receiver might be a handheld unit and also have an algorithm and display suggesting to the patient directly the current status and which actions to take.

A method according to another embodiment of the present invention is described for insertion of and establishing a electrical cardiac stimulator system, such as a pacemaker (PM) system, without leads or battery by means of converting kinetic energy from the heart 1 to electricity and using the a certain amount of the electricity produced for stimulating the heart 1 electrically securing a safe heart rhythm. The same method is applied for positioning of electrical cardiac stimulator devices implemented as defibrillation devices.

First access to the vein system is established by means of puncturing a large vein with a needle, such veins might be the cubital arm vein, the cephalic vein, the internal jugular vein 80, the subclavian vein, the femoral vein 82 or any other vein large enough. A guide wire 76 is then inserted and an introducer sheath 78 with a hemostatic valve is placed over the guide wire 76. Subsequently the guide wire 76 is withdrawn. Then a diagnostic catheter 102 is inserted to a location intended for positioning the device. For instance for LV pacing, the catheter may be inserted in the vein system through the coronary sinus 2 and the great cardiac vein 4 into smaller branches along the lateral wall of the left ventricular wall 26, the marginal branches. Other positions in the vein system would be in the anterior inter-ventricular vein on the front of the heart 1 or in the middle cardiac vein 10 behind the heart 1 between the left and the right ventricle.

Once the diagnostic catheter 102 is in position an angiogram of the vein system is achieved using contrast dye. By interpreting the image from the angiogram of the vein, the proper position for the device is decided. A guide wire 76 is now advanced to the selected position in the vein and beyond, whereupon the diagnostic catheter 102 is withdrawn, leaving the guide wire 76 in position. Over the guide wire 76 a guiding catheter is advanced to the deployment site or adjacent. Now the delivery system 92 is advanced over the guide wire 76 but inside the guiding catheter to the desired site. If the device is kept inside the delivery system 92 by means of a restraining catheter, this is now retracted, exposing the device that is expanding inside the vein and fixating itself there, or in case the device has tines 56 the tines 56 will attach to the vein wall, keeping the device strongly fixated. In case the device has a screw 58 for fixation in the tissue, the delivery system 92 is rotated in the proper direction until the screw 58 is solidly attached to the tissue. If the device has tines 56 for fixation they will engage the vein wall for secure anchoring. If the device is to be deployed in a cavity like the RV 62, LV 64, the right atrium 22 or the appendage of the right atrium 12, the same actions as above are executed until the guiding catheter and the delivery system 92 is in position inside the cavity. The device is advanced and in case of a screw attachment the delivery system 92 is rotated in the proper direction until the device has a strong attachment in the wall. In case the device has fixation tines 56 on the outside a place between the papillary muscles 28 or the muscular trabecles is located where the tines 56 get a good attachment and then the device is released from the delivery system 92 by retracting the delivery catheter 94 from over the device. In case the electrical cardiac stimulator system comprises several electrical cardiac stimulator devices, the procedure described above is repeated for each of the device members of the system by means of repositioning the guide catheter in the desired positions until all the devices in the system have been deployed. Once all electrical cardiac stimulator device, such as pacemaker, for example pace maker unit 70, and defibrillator devices, are in the proper positions the movements of the heart 1 will induce a certain amount of electricity in each of the devices. The devices are now able to communicate with the others. One of the devices, for instance an electrocardiogram detecting device may take the lead and run the operation of the system. The transmitting system of each of the devices or the leading device only will send the information to a receiver or a communication unit 7 outside of the body for interpretation and setting mode of operation by means of transmitting back to the device(s). The receiver outside of the body may be part of or connected to a mobile terminal or a fix-net telephone line for direct communication to a physician or a nurse for monitoring purposes and for taking the right actions. For instance most mobile terminals in the form of mobile telephones have an integrated Bluetooth wireless communication port. Embodiments of the intra cardiac device having a Bluetooth transmitter or transceiver may directly connect to such a mobile telephone according to a simple pairing routine matching the phone and the implanted device for communication. Once this link is established, data communicated via the Bluetooth link may easily be forwarded to or received via the mobile networks connection of the mobile phone enabling a multitude of operations including maintenance actions or reprogramming of the implanted devices.

The external receiver communicating wirelessly with the implanted intra cardiac device may also communicate information via a distributed network, like the Internet, e.g. to a physician for examination.

The external receiver might also be a part of or connected to intensive care monitors or telemetry systems. In the first case data from the intra cardiac devices may be displayed on the intensive care monitor. Often intensive care monitors are embedded in a network providing e.g. data storage, print outs etc., or even access to and from a Hospital Information System.

Connecting intra cardiac devices of embodiments of the invention wirelessly to telemetry systems provides a number of advantages compared with today's telemetry systems. Especially the patient telemetry units do no longer need ECG electrodes taped to the patient. Existing telemetry systems may be used with a simple transceiver outside the patient body managing communication both with the implanted intra cardiac device(s) and the fixed installed telemetry system. In this manner a convenient continuous monitoring of a patient is provided right away from the end of implantation. This may contribute to cost saving in healthcare as patients that have undergone cardiac surgery may be directly submitted to non-critical care units.

The invention may be implemented in any suitable form, and the elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units.

Although the present invention has been described above with reference to specific embodiments, it is not intended to be limited to the specific form set forth herein. Rather, the invention is limited only by the accompanying claims, and other embodiments than the specific above are equally possible within the scope of these appended claims.

In the claims, the term "comprises/comprising" does not exclude the presence of other elements or steps. Furthermore, although individually listed, a plurality of means, elements or method steps may be implemented. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A leadless, batteryless, self-contained, intra cardiac device for heart function intervention, said device comprising:
   an energy converting means for transforming kinetic energy into electrical energy, wherein said energy converting means produces an electrical conversion signal when transforming kinetic energy from heart tissue movement into electrical energy and powers said intra cardiac device with said electrical energy and derives measured data in respect of heart function from said electrical conversion signal when the device is in use; and
   a wireless transmitter or transceiver that transmits said measured data to a data receiving device.

2. The device according to claim 1, wherein said energy converting means comprises a magnet, movable relative a coil that transforms said kinetic energy into said electrical energy and produces said electrical conversion signal.

3. The device according to claim 1, wherein said energy converting means comprises a rotatable pendulum communicating with a magnet that is rotatable relative a coil for transforming said kinetic energy into said electrical energy and obtaining said electrical conversion signal.

4. The device according to claim 1, wherein said energy converting means comprises a piezo-electric energy converter for transforming said kinetic energy into said electrical energy and obtaining said electrical conversion signal.

5. The device according to claim 1, further comprising a capacitor to store said electrical energy for use by said device.

6. The device according to claim 1, further comprising fixation means for attachment of said device in or at the heart, wherein said fixation means is selected from the group consisting of a stent, tines, hooks, a screw, eyelets, and a suture.

7. The device according to claim 1, wherein a surface of said device comprises an elutionable steroid.

8. The device according to claim 1, wherein said device wirelessly transmits device function related data, administrative data, programmed data, cardiac stimulation pacing rate, defibrillation energy, and/or power unit condition via said wireless transmitter or transceiver.

9. The device according to claim 1, wherein said device is an electrical cardiac stimulator device, an implantable pacemaker, a cardioverter defibrillator, or a defibrillator.

10. The device according to claim 1, wherein said energy converting means derives said measured data from a characteristic voltage and current over time of said electrical conversion signal.

11. The device according to claim 10, further comprising at least one electronic circuit that comprises a pacing algorithm and/or a defibrillating algorithm.

12. The device according to claim 1, and further comprising a positive electrode and a negative electrode.

13. The device according to claim 12, wherein said positive and negative electrodes are configured to obtain electrical heart signals.

14. The device according to claim 12, wherein said electrical energy is stored in an energy storage means when said intra cardiac device is in use, and wherein said energy storage means is configured to provide energy stored therein for cardiac stimulation via said positive and negative electrodes when electrical heart signals are not obtained via said positive and negative electrodes.

15. The device according to claim 12, wherein said positive and negative electrodes are made of copper or steel or a polymer.

16. The device according to any of claim 12, wherein at least one of said positive and negative electrodes is covered with porous material.

17. The device according to claim 16, wherein said porous material is activated carbon, sintered platinum-iridium or sputtered titanium-nitride.

18. The device according to claim 1, wherein said measured data is selected from the group consisting of heart rate, heart movement amplitude, heart movement acceleration, and combinations thereof.

19. The device according to claim 1, wherein said heart tissue is heart muscle.

20. A system comprising said intra cardiac device according to claim 1 and said data receiving device.

21. The system according to claim 20, wherein said data receiving device is an extracorporeal receiver located outside a patient's body.

22. The system according to claim 20, wherein said data receiving device is located in a mobile terminal, a mobile telephone, a fix-net telephone, an intensive care monitor, a pacemaker, a defibrillator, an infusion pump, or a transceiver of a telemetry system.

23. The system according to claim 20, wherein said intra cardiac device according to claim 1 is a first intra cardiac device and said data receiver is located in a second intra cardiac device according to claim 1.

24. The system according to claim 20, wherein said wireless transmitter or transceiver transmits a signal via radio transmission, Bluetooth®, ZigBee®, ultrasound or combinations thereof.

25. The system according to claim 20, further comprising a delivery system, said delivery system comprising an introducer sheath, a guide wire, a diagnostic catheter, and a delivery catheter.

26. A method of treatment of heart blocks and/or arrhythmias, said method comprising:
   transforming kinetic energy from heart movement into electrical energy using a first device according to claim 1;
   deriving information obtained from said electrical energy related to said heart movement by the use of said first device; and obtaining electrical heart signals from said device, and stimulating the heart electrically by said first device or a second device according to claim 1 with at least a part of said electrical energy.

27. The method according to claim 26, wherein said stimulating the heart electrically is by said second device and said first intra cardiac device communiCates with said second device.

28. The method according to claim 27, wherein said first device acts as a master device and the second device acts as a slave device.

* * * * *